United States Patent
Park et al.

(10) Patent No.: US 10,160,766 B1
(45) Date of Patent: Dec. 25, 2018

(54) BENZOPYRANYL TETRACYCLE COMPOUND AND PHARMACEUTICAL COMPOSITION HAVING EXCELLENT ANTI-INFLAMMATORY EFFECT COMPRISING THE SAME

(71) Applicants: Spark Biopharma, Inc., Seoul (KR); Seoul National University R&DB Foundation, Seoul (KR)

(72) Inventors: Seung Bum Park, Seoul (KR); Wan Sang Cho, Daejeon (KR); Ja Young Koo, Seoul (KR)

(73) Assignees: Spark Biopharma, Inc., Seoul (KR); Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 15/800,767

(22) Filed: Nov. 1, 2017

(51) Int. Cl.
*A61K 31/41* (2006.01)
*C07D 491/00* (2006.01)
(Continued)

(52) U.S. Cl.
CPC .......... *C07D 491/147* (2013.01); *A61P 29/00* (2018.01); *A61P 37/00* (2018.01)

(58) Field of Classification Search
CPC ...... C07D 491/147; A61P 29/00; A61P 37/00; A61K 31/41
(Continued)

(56) References Cited

PUBLICATIONS

Zhu et al, Construction of Polyheterocyclic Benzopyran Library with Diverse Core Skeletons through diveristy-Oreientaerd synthesis pathway: Part II, ACS Combinatorial Science , 2012, 14(2), p. 124-134, abstract pp. 1-5. (Year: 2012).*

(Continued)

*Primary Examiner* — Taylor V Oh
(74) *Attorney, Agent, or Firm* — Mintz Levin Cohn Ferris Glovsky and Popeo, P.C.; Kongsik Kim; Moonkyoung Um

(57) ABSTRACT

The present invention relates a novel compound represented by the following Formula 3 or Formula 5, and a pharmaceutical composition having superior anti-inflammatory effect comprising the above. The above compound inhibits the translocation of HMGB1 form nucleus to cytosol, and then has remarkable effect of treating or preventing inflammatory disease, especially sepsis.

[Formula 3]

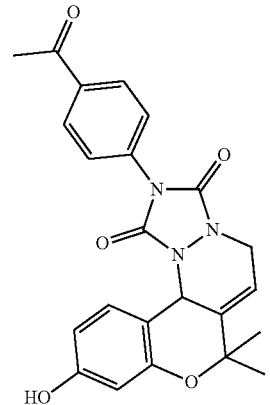

[Formula 5]

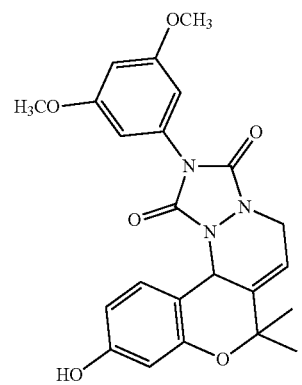

3 Claims, 11 Drawing Sheets

(51) Int. Cl.
*C07D 491/147* (2006.01)
*A61P 37/00* (2006.01)
*A61P 29/00* (2006.01)

(58) Field of Classification Search
USPC .................................. 544/233, 247; 514/383
See application file for complete search history.

(56) References Cited

PUBLICATIONS

Cho et al, Treatment of Sepsis Pathogenesis with High Mobility Group Box Protein 1-Regulating Anti-inflammatory Agents, Journal of Medicinal Chemistry, Dec. 2016, 60, p. 170-179. (Year: 2016).*

* cited by examiner

BENZOPYRANYL TETRACYCLE COMPOUND AND PHARMACEUTICAL COMPOSITION HAVING EXCELLENT ANTI-INFLAMMATORY EFFECT COMPRISING THE SAME

TECHNICAL FIELD

The present invention relates to novel compounds having benzopyran structure, their use and pharmaceutical composition comprising the above. Specifically, it relates to novel benzopyranyl tetracycle compounds, and pharmaceutical composition having excellent anti-inflammatory effect comprising the above.

BACKGROUND ART

Inflammation is a pathological condition of an abscess caused by foreign infectious agents (bacteria, fungi, virus, various kinds of allergens, etc.). For example, when foreign bacteria invade into and proliferate in a tissue, the leukocytes of the body recognize and actively attack the proliferating foreign bacteria, during which leukocytes die and bacteria are killed by the leukocytes. The dead leukocytes and bacterial lysates accumulate in the tissue, forming an abscess.

The abscess formed by inflammation can be treated through anti-inflammation activity. Anti-inflammation activity refers to a process that reduces inflammation in which the proliferation of the foreign agent, such as bacteria, is inhibited with the aid of an anti-inflammatory agent, for example, an antibacterial agent, or in which macrophages are activated to digest and excrete the foreign materials accumulated in the abscess.

Inflammation refers to a biological protective response of tissues to harmful stimuli. Inflammation is a protective attempt by the organism to remove the injurious stimuli and to initiate the healing process for rehabilitating the cells or tissues on which organic lesion has been imposed by the invasion of the stimuli. Factors involved in these serial processes are local vascular tissues, various tissue cells of the body fluid, immune cells, etc.

Like the inflammation that is normally induced by foreign pathogens, the defense mechanism for protecting the body is indispensable for survival. However, temporally or spatially inappropriate inflammatory responses play a great role in causing a broad spectrum of diseases including those that are not believed to be related with leukocytes, such as arthritis and Alzheimer disease, as well as those apparently induced by leukocyte components, such as autoimmune diseases, asthma, and atherosclerosis.

In such inflammatory diseases, leukocytes are incited to rush to the affected tissue upon an autoimmune response where an antibody inadvertently recognizes a host protein, or by inappropriate triggers, such as accumulated tissue injury, for example, apoptotic bodies of permanent cells, extracellular cholesterol deposits, or intra-pulmonary particulates. The leukocytes, although crowded, cannot dispose of all the triggers (for example, leukocytes cannot remove or kill all autoimmune antigen-expressing host cells, or cannot phagocyte too excessively large particles from the host cells).

Hence, such diseases occasionally become chronic and continue to release inflammatory cytokines, dispatching additional leukocytes to unnecessary sites where chronic inflammation is thus formed. This inflammatory response is reported to induce chronic progressive diseases such as arteriosclerosis, obesity, insulin resistance, rheumatoid arthritis, glomerulonephritis, cancer, etc. and to play an important role in the progression of senescence.

Sepsis is a systemic inflammatory response caused by microbial infection, and may be result in severe sepsis or septic shock.

When the pathophysiology of sepsis is associated with hypoperfusion, hypotension, and organ dysfunction, it is termed as severe sepsis, which occurs in approximately 10% of all intensive care unit patients in the U.S.

Although numerous therapeutic approaches to sepsis have been advanced, the mortality rate of severe sepsis is nearly 20%. Furthermore, the annual hospital healthcare cost for patients with severe sepsis in the U.S. is the highest among all diseases and was around $20 billion.

The biggest obstacle to the discovery of therapeutics for sepsis is its diverse etiology among patients. The heterogeneous patterns of sepsis pathogenesis depend on the pathogenic organisms and sites of infection. The diverse characteristics of sepsis pathogenesis have prompted researchers to study the molecular mechanism of sepsis progression based on systemic inflammatory responses.

Various methods have been tried, for example, a method of treating sepsis using antibiotics or a method of inhibiting mediators such as TNF-α, IL-6 and IL-1, which mediate or accelerate inflammation response. However, those methods have not yet remarkably improved the survival rate of sepsis patients.

Sepsis occurs when immune responses are overactivated, including intractable inflammatory responses associated with imbalanced cytokine production. In addition, the subsequently unmanaged pro-inflammatory cytokine cascade results in whole body shock.

Furthermore, tumor necrosis factor (TNF)-α and interleukin-(IL)-1β are two major pro-inflammatory cytokines involved in sepsis and their secretion is regulated by positive feedback during systemic inflammatory responses.

When the secreted cytokines circulate in the whole body, large amounts of cytokines are produced, resulting in septic shock and secondary multiple organ dysfunctions. Therefore, therapeutic approaches to antagonize the production of these cytokines have been used for the treatment of sepsis.

For example, an anti-TNF-α antibody underwent large-scale clinical trials but was discontinued because it lacked efficacy. Literature reports suggest these failures might have been caused by two reasons.

First, because the production of TNF-α and IL-1β peaks at the early stage of systemic inflammation, it is difficult to reverse the enhanced cytokine production without inhibiting the early stage of pathogenesis.

Second, the continuous inflammatory stimuli unexpectedly restored the TNF-α level after the treatment with anti-TNF-α antibody.

On the other hand, HMGB1 (High mobility group box 1) is a constantly expressed nuclear protein, which is secreted from Gangrene cells and surrounding cells. where tissue damage occurs. There are one or more than one receptors for extracellular HMGB1. The receptor signaling induces cell division and cell migration, activates inflammation, and initiates an immune response. The cells that secrete HMGB1 include monocytes, macrophages, and human umbilical vein endothelial cells. HUVEC). Further, when HMGB1 is activated and secreted, it results in severe vascular inflammation, sepsis and death.

HMGB1 binds to RAGE (receptor for advanced glycation end products) or pattern recognition receptors (TLR2, TLR4), and then induces the expression of adhesion molecules (VCAM-1, ICAM-1, E-selectin) on endothelial cells.

An inflammatory response in an endothelial cell is initiated by HMGB1, which increases the secretion of TNF and IL-6, and induces phosphorylation of NFC-kB, ERK, and ERK-2.

It is known that HMGB1 is detected in the serum of sepsis patients and the level of HMGB1 is significantly increased in the serum of serious sepsis patients. It also is known that when the concentration of HMGB1 increases in the serum of severe sepsis patients, the possibility of the death increases. Thus, HMGB1 is the target molecule for the prevention or treatment of sepsis or other vascular inflammatory diseases.

High mobility group box protein 1 (HMGB1) has been identified as a late-stage mediator of inflammatory responses. When damaged cells undergo necrotic death, HMGB1 is released into the extracellular milieu, alerting adjacent cells to the damage. Interestingly, in immune cells such as macrophages, HMGB1 is actively secreted as a pro-inflammatory cytokine during systemic inflammatory responses.

Previous reports have indicated that secreted HMGB1 plays an important role in regulating the production of other pro-inflammatory cytokines. In this context, it has been reported that the inhibition of HMGB1 secretion successfully ameliorated the pathogenesis of sepsis in an in vivo cecal ligation and puncture (CLP) mouse model, the gold standard animal model in the field of sepsis study (Proc. Natl. Acad. Sci. U.S.A. 2004, 101, 296-301).

Briefly, the CLP mouse model is established by performing a surgical procedure to the cecum, which is the organ where the resident enteric microbiome exists. Ligating the cecum and puncturing the end with a needle causes endotoxemia by inducing polymicrobial contamination in the abdominal cavity toward the circulatory system.

This action subsequently initiates a systemic inflammatory response, namely sepsis. Regarding the role of HMGB1 in sepsis, previous researchers reported that the anti-HMGB1 antibody abrogated the lethality of the CLP-induced mouse model by inhibiting the release of HMGB1.

Furthermore, a known autophagy modulator, (−)-epigallocatechin-3-gallate (EGCG), has been studied for the prevention of lipopolysaccharide (LPS)-induced HMGB1 release by triggering the degradation of cytosolic HMGB1, thereby boosting the autophagic process.

Present inventors discovered a novel small molecule, inflachromene (ICM, Compound 1d), that inhibits the activation of BV-2 microglia-like cells, by screening drug-like compound library via Diversity-Oriented Synthesis (Korean Patent No. 10-1645942).

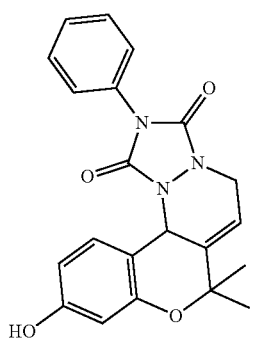

(ICM, Compound 1d)

On the basis of our efforts on target identification using the fluorescence difference in two-dimensional gel electrophoresis (FITGE) method, the present inventors revealed HMGB1 and HMGB2 as the target proteins of ICM, and the subsequent biochemical and biophysical studies confirmed that ICM inhibits the secretion of HMGB1 and HMGB2 in microglia via the modulation of their posttranslational modifications.

The present inventors prepared various candidate compounds by changing the substituents of the above compound, ICM, and finally found the novel compounds having much more excellent anti-inflammation effect, when compared with the compound, ICM, based on the structure-activity relationship research.

The present inventors confirmed the anti-inflammation effect on the candidate compounds.

That is, the present inventors tested the anti-inflammation effect on the candidate compounds, and further searched the mechanism of inhibiting the movement and secretion of HMGB1 causing inflammation. Specifically, the present invention has been completed by testing and comparing the survival rates, etc. after administering Compound ad and the candidate compounds in CLP mouse model.

In addition, the present inventors provide novel compounds having superior therapeutic effect on sepsis, by confirming that the control of HMGB1 release is a promising strategy for treating sepsis.

SUMMARY

The present provides novel compounds having superior effect, based on the structure-activity relationship research.

The above novel compounds provide a new method of treating inflammation. Especially, the above novel compounds provide a new method of treating or preventing sepsis.

Especially, the above novel compounds inhibit HMGB1, which acts as a late-stage mediator of inflammatory response, and then show superior effect on inflammation, especially sepsis, to currently used therapeutic agents.

The present invention provides a compound represented by the following Formula 1, or its pharmaceutically acceptable salt:

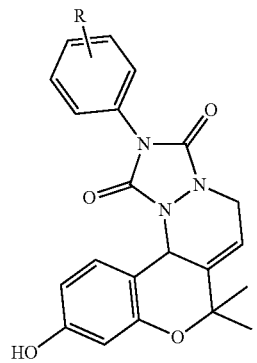

[Formula 1]

wherein,

R is substituted or unsubstituted $C_{1-8}$ alkyl; substituted or unsubstituted $C_{1-8}$ alkoxy; substituted or unsubstituted $C_{1-8}$ dialkoxy; substituted or unsubstituted $C_{1-8}$ alkylcarbonyl; methylenedioxy or ethylenedioxy.

Preferably, the compound represented by Formula 1 may be the compounds represented by Formulae 2 to 5 (Compounds 2i to 2l).

| Formula | Compound | Structure |
|---|---|---|
| 2 | 2i | 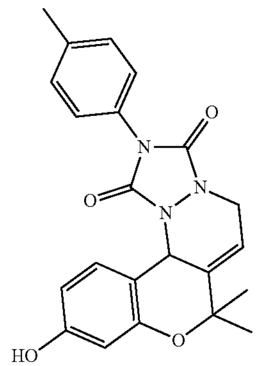 [SMILES: Cc1ccc(-n2c(=O)n3n(c2=O)C2C(=CC3)C(C)(C)Oc3cc(O)ccc32)cc1] |
| 3 | 2j | 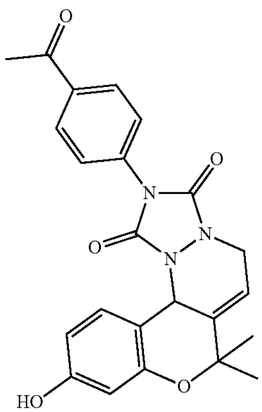 [SMILES: CC(=O)c1ccc(-n2c(=O)n3n(c2=O)C2C(=CC3)C(C)(C)Oc3cc(O)ccc32)cc1] |
| 4 | 2k | 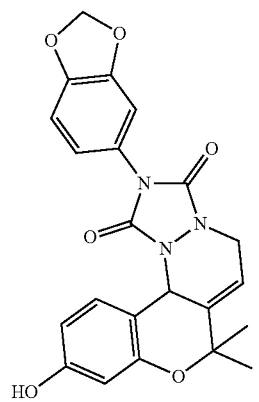 [SMILES: CC1(C)Oc2cc(O)ccc2C2C1=CCn1c(=O)n(-c3ccc4c(c3)OCO4)c(=O)n12] |
| 5 | 2l | 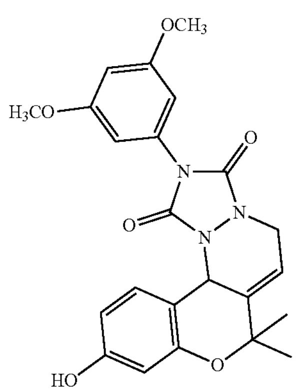 [SMILES: COc1cc(OC)cc(-n2c(=O)n3n(c2=O)C2C(=CC3)C(C)(C)Oc3cc(O)ccc32)c1] |

Formula 3 (Compound 2j) or Formula 5 (Compound 2l), or its pharmaceutically acceptable salt is the most preferable compound which is represented by Formula 1.

Further, the present invention provides a method of treating inflammatory disease, comprising administering to a subject in need a compound of Formula 3 or 5.

Further, the present invention provides a method of treating sepsis, comprising administering to a subject in need a compound of Formula 3 or 5.

The present invention provides a method of inhibiting inflammatory responses by preventing HMGB1 which is translocated from nucleus to cytosol and released to the extracellular milieu.

Especially, since HMGB1 acts as a late-stage inflammatory mediator, the novel compounds of the present invention, which inhibit the movement and release of HMGB1, may be used to the patients who are not well treated at the early stage of the inflammatory responses.

Further, the novel compounds of the present invention reduce the secretion of IL-6 and increase the survival rate of patients. Thus, the novel compounds are able to be used as superior therapeutic agents of inflammatory diseases.

The novel compounds of the present invention show superior pharmacokinetic properties such as improved solubility, stability and PK data, and then have pharmaceutical advantages when prepared as a medicine

DETAILED DESCRIPTION

Figure 1:
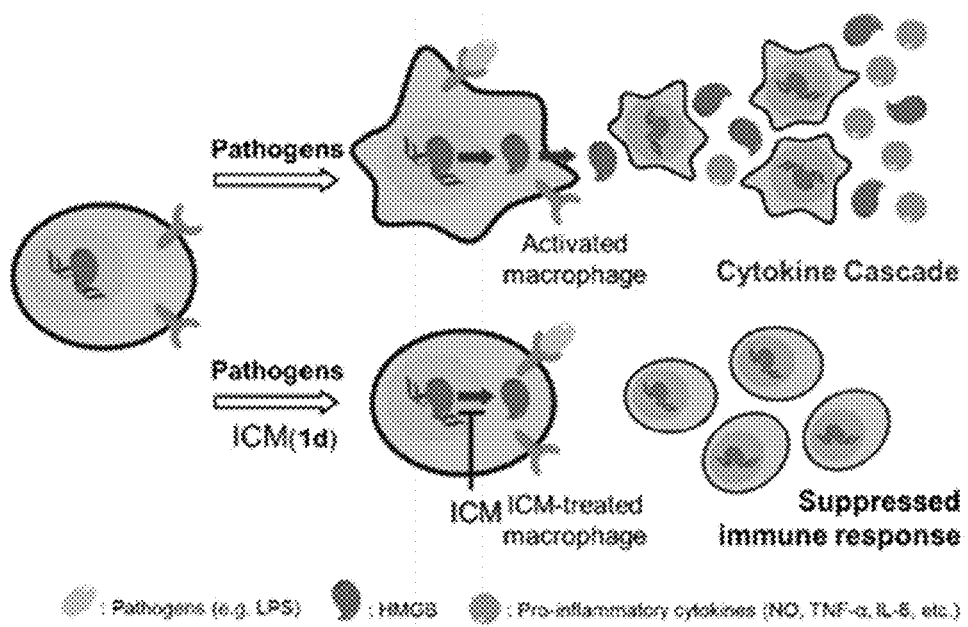
FIG. 1 shows the pathway of inhibiting the inflammatory response by Compound 1d.

The present inventors found that Compound 1d inhibiting HMGB1 in CLP mouse model effectively prevents the pathway of sepsis. In this regard, the present inventors prepared the candidate compounds having the structure similar to that of Compound 1. In addition, the present inventors selected the compounds having superior anti-inflammatory effect based on the candidate compounds.

As a result, the present inventors have invented the novel compounds having the most remarkable anti-inflammatory effect, based on the structure-activity relationship research and various experimental results.

The present invention provides the compound represented by the following Formula 1, or its pharmaceutically acceptable salt.

[Formula 1]

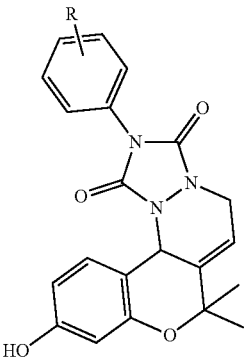

Wherein,

R is substituted or unsubstituted $C_{1-8}$ alkyl; substituted or unsubstituted $C_{1-8}$ alkoxy; substituted or unsubstituted $C_{1-8}$ dialkoxy; substituted or unsubstituted $C_{1-8}$ alkylcarbonyl; methylenedioxy or ethylenedioxy.

Preferably, the compound represented by Formula 1 may be the compounds represented by Formulae 2 to 5 (Compounds 2i to 2l).

Formula 3 (Compound 2j) or Formula 5 (Compound 2l), or its pharmaceutically acceptable salt is the most preferable compound which is represented by Formula 1.

[Formula 3]

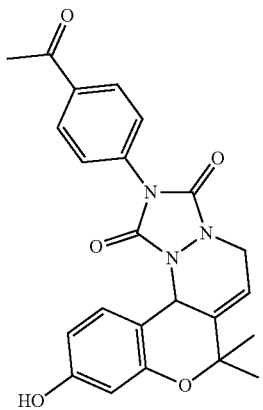

[Formula 5]

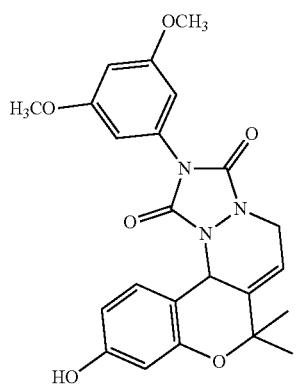

The present invention provides a method of treating inflammatory disease, comprising administering the compound of Formula 3 or 5, or its pharmaceutically acceptable salt to a subject in need.

The present invention is characterized in that the novel compounds inhibit HMGB1 which is an inflammation mediator Specifically, the novel compounds inhibit the phosphorylation or acetylation of HMGB1 and then prevent the translocation of HMGB1 from the nucleus to the cytosol. As a result, the release of HMGB1 to the extracellular milieu is inhibited.

Inflammation is a protective attempt by the organism to remove the injurious stimuli and to initiate the healing process for rehabilitating the cells or tissues on which an organic lesion has been imposed by the invasion of the stimuli. Factors involved in these serial processes are local vascular tissues, various tissue cells of the body fluid, immune cells, etc.

The inflammation response which is normally induced by foreign pathogens is the defense mechanism for protecting the body. However, if induced, excessively abnormal inflammation causes a broad spectrum of diseases including chronic diseases, such as gastritis, colitis, rheumatoid arthritis, nephritis, hepatitis, pancreatitis, sepsis, seizure, cancer, multiple sclerosis, Alzheimer's disease, Parkinson's disease, and Huntington's disease, and neuroinflammatory diseases, such as brain injury in an acute stage including stroke, trauma, etc. Inter alia, sepsis, seizure and cancer are affected by HMGB.

Hence, the pharmaceutical composition comprising the compound of Formula 3 or 5 can be used for the treatment of at least one inflammation-related disease selected from the group consisting of gastritis, colitis, rheumatoid arthritis, nephritis, hepatitis, pancreatitis, sepsis, seizure, multiple sclerosis, Alzheimer's disease, Parkinson's disease, Huntington's disease, amyotrophic lateral sclerosis (Lou Gehrig's disease), stroke, trauma, spinal cord injury, and cancer.

Especially, the pharmaceutical composition comprising the novel compound of Formula 3 or 5 can be used as a medicine of treating or preventing sepsis.

The present invention relates to a method of treating inflammatory disease, comprising administering the compound of Formula 3 or 5 to a subject in need.

The present invention relates to a method of treating sepsis, comprising administering the compound of Formula 3 or 5 to a subject in need.

EXAMPLES

A better understanding of the present invention may be obtained through the following examples which are set forth to illustrate, but are not to be construed as limiting the present invention.

Example 1: Preparation of Compounds 1a to 1j

Compounds 1a to 1j were prepared according to the following Reaction 1.

[Reaction 1]

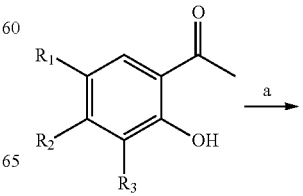

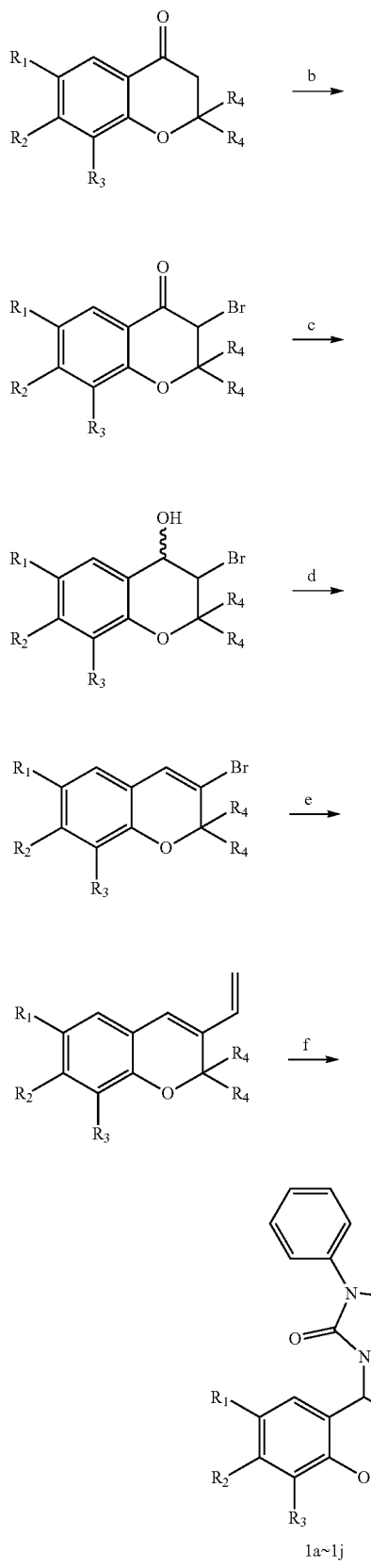

In the step a), hydroxyacetophenone having appropriate substituents $R_1$, $R_2$, and $R_3$ was added with ketone and pyrrolidine in ethanol (EtOH) solvent, and refluxed.

In step b), $CuBr_2$ was added in the mixture solvent $EtOAc/CHCl_3/MeOH$ and refluxed.

In step c), $NaBH_4$ was added in EtOH solvent, and the reaction was conducted at 40° C.

In step d), p-TsOH was added in toluene solvent and the reaction was conducted at 70° C.

In step e), the reaction was conducted at 70° C. in the mixture solvent $EtOH/toluene/H2O$ in the presence of vinyl-boronic acid dibutyl ester, $Na_2CO_3$, and $Pd(PPh_3)_4$.

In step f), phenyltriazolinedione was added in toluene solvent, and the reaction was conducted at room temperature.

In the above preparation method, it is preferable to protect the $R_2$ or $R_3$ functional group with a triisopropylsilyl protecting group before the step d), in case when the $R_2$ or $R_3$ functional group is OH (1d, 1h, 1i, 1j).

The above was deprotected with a hydrofluoric acid-pyridine mixture in THF solvent immediately after step f) to obtain the final compound.

In case when the $R_2$ functional group is N-methylamino (1b), it is preferable to protect it with Boc protecting group before step e). The above was deprotected with trifluoroacetic acid in dichloromethane solvent after f) step to obtain the final compound.

When the $R_4$ functional group is N-propyl-4'-piperidyl (1i) or N-acetyl-4'-piperidyl (1j), the N-Boc-piperidinone protected with the Boc protecting group was used as a ketone in step a), and further steps b) to f) were proceeded.

The Boc protecting group was first deprotected with trifluoroacetic acid in a dichloromethane solvent prior to the deprotection of the $R_2$ functional group The reductive amination reaction was carried out using propionaldehyde and triacetoxyborohydride in a dichloroethane solvent in order to obtain the final product (1i) or the acetylation reaction was carried out using an acetic anhydride and a diisopropylethylamine base in a dichloromethane solvent to order to obtain the final compound (1j).

The structures, molecular weights, MS analysis values and NMR of the compounds 1a to 1j prepared through the above reaction schemes are shown in Table 1 below.

TABLE 1

| Compound | Structure | Molecular Weight | MS Analysis Value (Molecular Weight +H⁺) | NMR |
|---|---|---|---|---|
| 1a | 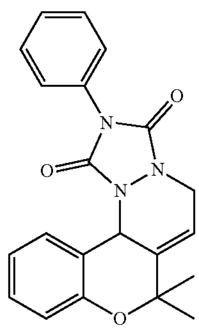 [SMILES: CC1(C)Oc2ccccc2C2C1=CCn1c(=O)n(-c3ccccc3)c(=O)n12] | 361.40 | 361.1429 [M]⁺ | ¹H-NMR (500 MHz, CDCl₃): δ 7.64 (d, J = 7.5 Hz, 2H), 7.53 (t, J = 7.5 Hz, 2H), 7.42 (t, J = 7.5 Hz, 1H), 7.22 (t, J = 7.5 Hz, 1H), 7.06 (d, J = 7.5 Hz, 1H), 6.96 (t, J = 7.5 Hz, 1H), 6.90 (d, J = 8.0 Hz, 1H), 5.80 (t, J = 2.5 Hz, 1H), 5.73 (s, 1H), 4.30 (dd, J = 16.5 and 5.0 Hz, 1H), 4.11 (dt, J = 16.5 and 2.5 Hz, 1H), 1.62 (s, 3H), 1.57 (s, 3H); ¹³C-NMR (125 MHz, CDCl₃): δ 153.8, 153.4, 151.6, 138.2, 131.4, 129.4, 129.3, 128.5, 125.6, 124.3, 123.5, 121.9, 118.2, 112.9, 79.4, 50.7, 44.3, 28.2, 27.2 |
| 1b | 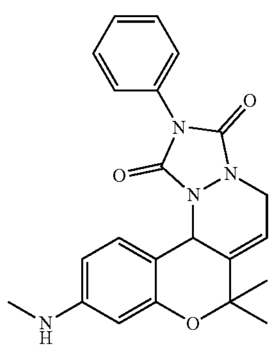 [SMILES: CNc1ccc2c(c1)OC(C)(C)C1=CCn3c(=O)n(-c4ccccc4)c(=O)n3C12] | 390.44 | 391.09 | ¹H-NMR (500 MHz, CDCl₃): δ 7.64 (d, J = 7.5 Hz, 2H), 7.53 (t, J = 7.5 Hz, 2H), 7.43 (t, J = 7.5 Hz, 1H), 7.05 (t, J = 7.5 Hz, 1H), 6.85 (dd, J = 8.5 and 2.0 Hz, 1H), 6.81 (d, J = 2.0 Hz, 1H), 5.85 (t, J = 2.5 Hz, 1H), 5.73 (s, 1H), 4.30 (dd, J = 14.0 and 3.5 Hz, 1H), 4.10 (dt, J = 14.0 and 2.5 Hz, 1H), 3.22 (s, 3H), 1.62 (s, 3H), 1.60 (s, 3H), 1.46 (s, 9H) |
| 1c | 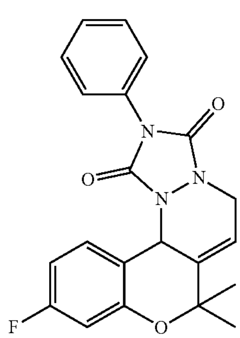 [SMILES: CC1(C)Oc2cc(F)ccc2C2C1=CCn1c(=O)n(-c3ccccc3)c(=O)n12] | 379.39 | 380.1409 | ¹H-NMR (500 MHz, CDCl₃): δ 7.62 (d, J = 7.5 Hz, 2H), 7.52 (t, J = 7.5 Hz, 2H), 7.45 (t, J = 7.5 Hz, 1H), 7.07 (t, J = 8.0 Hz, 1H), 6.66 (td, J = 8.5 and 2.5 Hz, 1H), 6.60 (dd, J = 8.5 and 2.5 Hz, 1H), 5.86 (t, J = 2.5 Hz, 1H), 5.70 (s, 1H), 4.30 (dd, J = 16.5 and 5.0 Hz, 1H), 4.11 (dt, J = 16.5 and 2.5 Hz, 1H), 1.60 (s, 3H), 1.59 (s, 3H); ¹³C-NMR (125 MHz, CDCl₃): δ 164.5, 162.5, 154.7, 153.9, 151.7, 137.2, 131.4, 129.5, 128.6, 125.6, 125.2(d), 119.6(d), 113.7, 108.8(d), 105.6(d), 79.7, 50.3, 44.4, 27.9, 27.0 |

TABLE 1-continued

| Compound | Structure | Molecular Weight | MS Analysis Value (Molecular Weight +H⁺) | NMR |
|---|---|---|---|---|
| 1d | 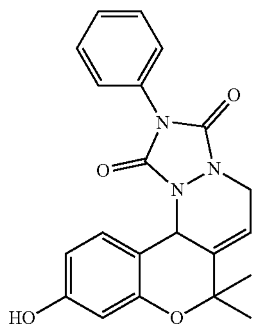 [SMILES: CC1(C)Oc2cc(O)ccc2C2C1=CCn1c(=O)n(-c3ccccc3)c(=O)n12] | 377.40 | 377.1380 [M]⁺ | $^1$H-NMR (500 MHz, acetone-d$_6$): δ 8.47 (br.s., 1H), 7.65 (d, J = 7.5 Hz, 2H), 7.53 (t, J = 7.5 Hz, 2H), 7.43 (t, J = 7.5 Hz, 1H), 6.98 (d, J = 8.5 Hz, 1H), 6.44 (dd, J = 8.5 and 2.5 Hz, 1H), 6.35 (d, J = 2.5 Hz, 1H), 6.02 (t, J = 2.5 Hz, 1H), 5.64 (s, 1 H), 4.25 (dd, J = 16.5 and 5.0 Hz, 1H), 4.14 (dt, J = 16.5 and 2.5 Hz, 1H), 1.61 (s, 3H), 1.57 (s, 3H); $^{13}$C-NMR (125 MHz, acetone-d$_6$): δ 159.2, 155.3, 155.0, 152.2, 138.0, 133.0, 129.6, 128.7, 126.7, 125.6, 116.3, 114.6, 109.4, 105.3, 79.8, 50.6, 45.2, 27.8, 27.2 |
| 1e | 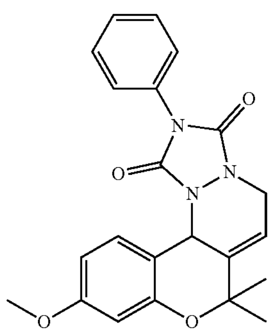 [SMILES: COc1ccc2c(c1)OC(C)(C)C1=CCn3c(=O)n(-c4ccccc4)c(=O)n3C12] | 391.43 | 391.16 [M]⁺ | $^1$H-NMR (500 MHz, CDCl$_3$): δ 7.63 (d, J = 7.5 Hz, 2H), 7.53 (t, J = 7.5 Hz, 2H), 7.43 (t, J = 7.5 Hz, 1H), 7.05 (d, J = 8.5 Hz, 1H), 6.52 (dd, J = 8.5 and 3.0 Hz, 1H), 6.45 (d, J = 3.0 Hz, 1H), 5.86 (t, J = 2.0 Hz, 1H), 5.74 (s, 1H), 4.31 (dd, J = 16.0 and 5.0 Hz, 1H), 4.12 (dt, J = 16.0 and 2.5 Hz, 1H), 3.77 (s, 3H), 1.62 (s, 3H), 1.61 (s, 3H); $^{13}$C-NMR (125 MHz, CDCl$_3$): δ 161.0, 154.5, 154.1, 151.7, 137.5, 131.5, 129.5, 128.5, 125.7, 124.9, 115.7, 113.1, 108.0, 103.3, 79.0, 55.6, 50.3, 44.5, 27.7, 27.0 |
| 1f | 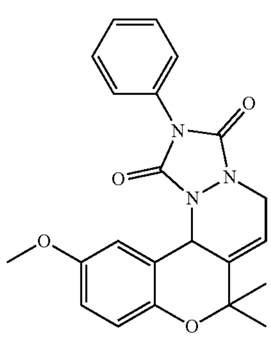 [SMILES: COc1ccc2c(c1)C1C(=CCn3c(=O)n(-c4ccccc4)c(=O)n31)C(C)(C)O2] | 391.43 | 392.10 | $^1$H-NMR (500 MHz, CDCl$_3$): δ 7.64 (d, J = 7.0 Hz, 2H), 7.53 (t, J = 7.0 Hz, 2H), 7.43 (t, J = 7.0 Hz, 1H), 6.86 (d, J = 8.0 Hz, 1H), 6.77 (d, J = 8.0 Hz, 1H), 6.61 (s, 1H), 5.76 (q, J = 2.5 Hz, 1H), 5.67 (s, 1H), 4.30 (dd, J = 16.5 and 5.0 Hz, 1H), 4.13 (dd, J = 16.5 and 2.5 Hz, 1H), 3.74 (s, 3H), 1.53 (s, 3H), 1.42 (s, 3H); $^{13}$C-NMR (125 MHz, CDCl$_3$): δ 154.9, 153.6, 151.6, 147.1, 139.3, 131.4, 129.4, 128.5, 126.1, 125.6, 119.0, 114.1, 112.6, 109.1, 79.6, 55.9, 51.2, 44.1, 28.4, 27.3 |

TABLE 1-continued

| Compound | Structure | Molecular Weight | MS Analysis Value (Molecular Weight +H+) | NMR |
|---|---|---|---|---|
| 1g | 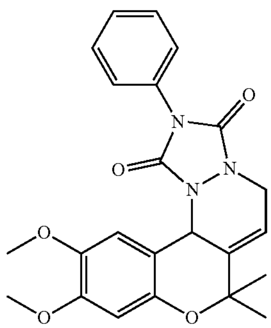 [SMILES: COc1cc2c(cc1OC)C1C(=CCn3c(=O)n(-c4ccccc4)c(=O)n31)C(C)(C)O2] | 421.45 | 422.11 | ¹H-NMR (500 MHz, CDCl$_3$): δ 7.60 (d, J = 7.5 Hz, 2H), 7.53 (t, J = 7.5 Hz, 2H), 7.43 (t, J = 7.5 Hz, 1H), 6.76 (s, 1H), 6.46 (s, 1H), 5.88 (t, J = 2.5 Hz, 1H), 5.74 (s, 1H), 4.32 (dd, J = 16.5 and 5.0 Hz, 1H), 4.13 (dt, J = 16.5 and 2.5 Hz, 1H), 3.83 (s, 3H), 3.78 (s, 3H), 1.61 (s, 3H), 1.59 (s, 3H) |
| 1h | 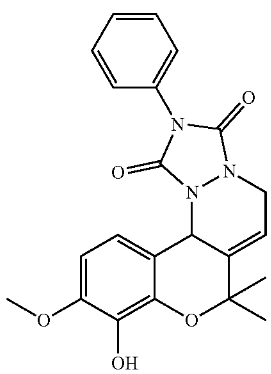 [SMILES: COc1ccc2c(c1O)OC(C)(C)C1=CCn3c(=O)n(-c4ccccc4)c(=O)n3C12] | 407.43 | 408.11 | ¹H-NMR (500 MHz, CDCl$_3$): δ 7.62 (d, J = 7.5 Hz, 2H), 7.52 (t, J = 8.0 Hz, 2H), 7.41 (t, J = 7.5 Hz, 1H), 6.58 (d, J = 9.0 Hz, 1H), 6.53 (d, J = 8.5 Hz, 1H), 5.84 (t, J = 2.5 Hz, 1H), 5.73 (s, 1H), 5.44 (br.s, 1H), 4.31 (dd, J = 16.5 and 5.0 Hz, 1H), 4.09 (dt, J = 16.5 and 2.5 Hz, 1H), 3.86 (s, 3H), 1.65 (s, 3H), 1.63 (s, 3H); ¹³C-NMR (125 MHz, CDCl$_3$): δ 154.0, 151.7, 147.5, 140.7, 138.0, 135.3, 131.4, 129.5, 128.6, 125.7, 117.9, 113.6, 113.4, 105.0, 80.4, 56.5, 50.4, 44.5, 28.0, 27.3 |
| 1i | 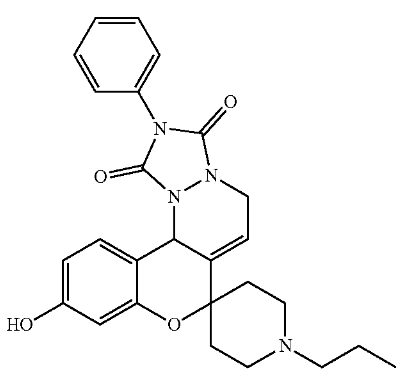 [SMILES: CCCN1CCC2(CC1)Oc1cc(O)ccc1C1C2=CCn2c(=O)n(-c3ccccc3)c(=O)n21] | 460.53 | 460.91 | ¹H-NMR (500 MHz, CDCl$_3$): δ 7.62 (d, J = 8.5 Hz, 2H), 7.52 (t, J = 7.5 Hz, 2H), 7.44 (t, J = 7.5 Hz, 1H), 6.93 (t, J = 9.0 Hz, 1H), 6.53 (dd, J = 8.5 and 2.0 Hz, 1H), 6.46 (d, J = 2.0 Hz, 1H), 5.92 (t, J = 2.5 Hz, 1H), 5.61 (s, 1H), 4.30 (dd, J = 16.5 and 5.0 Hz, 1H), 4.11 (dt, J = 16.5 and 2.5 Hz, 1H), 3.12 (q, J = 7.5 Hz, 2H), 2.92-2.89 (m, 2H), 2.34-3.39 (m, 2H), 2.18-2.03 (m, 2H), 1.87-1.78 (m, 2H), 1.37-1.32 (m, 2H), 1.23 (q, J = 7.5 Hz, 3H), 1.08 (d, J = 7.5 Hz, 18H), 1.01 (t, J = 7.5 Hz, 3H) |

TABLE 1-continued

| Compound | Structure | Molecular Weight | MS Analysis Value (Molecular Weight +H$^+$) | NMR |
|---|---|---|---|---|
| 1j | 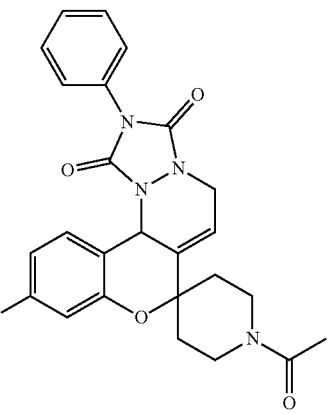 | 460.49 | 460.94 | $^1$H-NMR (500 MHz, CDCl$_3$): δ 7.63 (d, J = 7.5 Hz, 2H), 7.53 (t, J = 7.5 Hz, 2H), 7.42 (t, J = 7.5 Hz, 1H), 6.95 (d, J = 8.0 Hz, 1H), 6.51 (dd, J = 8.5 and 2.0 Hz, 1H), 6.48 (d, J = 2.0 Hz, 1H), 5.80 (t, J = 2.0 Hz, 1H), 5.68 (s, 1H), 4.32 (dd, J = 16.5 and 5.0 Hz, 1H), 4.12 (d, J = 16.5 Hz, 1H), 3.46-3.37 (m, 2H), 3.35-3.18 (m, 2H), 2.17-2.13 (m, 2H), 1.92-1.78 (m, 2H), 1.50 (s, 9H), 1.23 (q, J = 7.5 Hz, 3H), 1.08 (d, J = 7.5 Hz, 18H) |

Example 2: Preparation of Compounds 2a to 2o

Compounds 2a to 2o were prepared according to Reaction 2.

[Reaction 2]

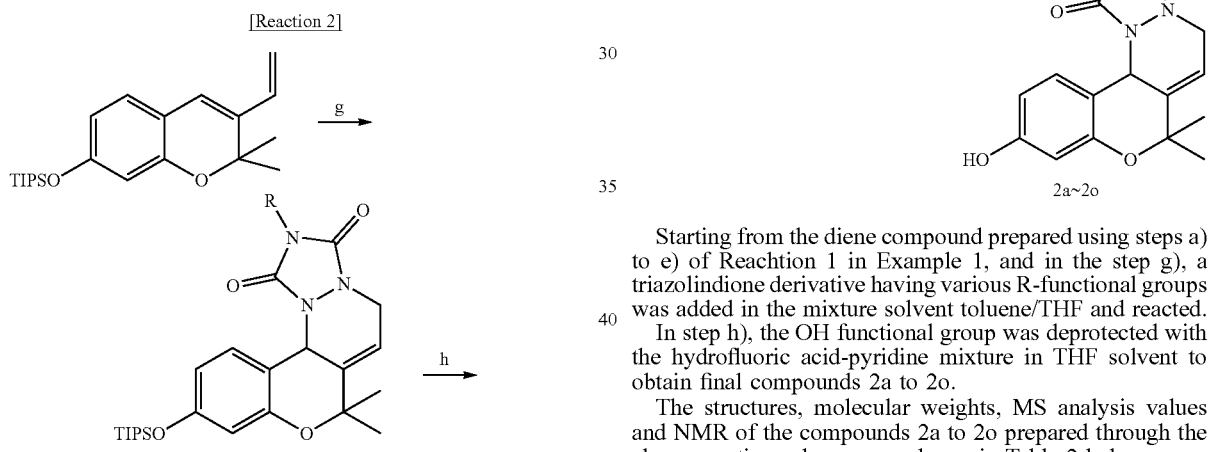

Starting from the diene compound prepared using steps a) to e) of Reachtion 1 in Example 1, and in the step g), a triazolindione derivative having various R-functional groups was added in the mixture solvent toluene/THF and reacted.

In step h), the OH functional group was deprotected with the hydrofluoric acid-pyridine mixture in THF solvent to obtain final compounds 2a to 2o.

The structures, molecular weights, MS analysis values and NMR of the compounds 2a to 2o prepared through the above reaction schemes are shown in Table 2 below.

TABLE 2

| Compound | Structure | Molecular Weight | MS Analysis Value (Molecular Weight +H$^+$) | NMR |
|---|---|---|---|---|
| 2a | 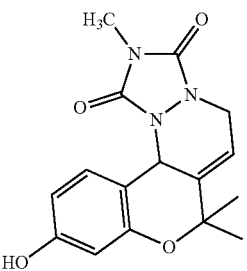 [SMILES: Cn1c(=O)n2n(c1=O)C1C(=CC2)C(C)(C)Oc2cc(O)ccc21] | 315.33 | 315.91 | $^1$H-NMR (500 MHz, CDCl$_3$): δ 6.82 (d, J = 8.5 Hz, 1H), 6.46 (dd, J = 8.0 and 2.5 Hz, 1H), 6.41 (d, J = 2.5 Hz, 1H), 5.77 (t, J = 2.5 Hz, 1H), 5.61 (s, 1H), 4.21 (dd, J = 16.5 and 5.0 Hz, 1H), 3.96 (dt, J = 16.5 and 2.5 Hz, 1H), 3.23 (s, 3H), 1.57 (s, 3H), 1.56 (s, 3H), 1.23 (q, J = 7.5 Hz, 3H), 1.08 (d, J = 7.5 Hz, 18H); $^{13}$C-NMR (125 MHz, CDCl$_3$): δ |

TABLE 2-continued

| Compound | Structure | Molecular Weight | MS Analysis Value (Molecular Weight +H⁺) | NMR |
|---|---|---|---|---|
| | | | | 157.3, 155.7, 154.2, 153.0, 137.9, 124.3, 116.6, 113.5, 112.9, 109.5, 79.0, 50.2, 44.3, 27.8, 27.1, 25.6, 18.1, 12.8. |
| 2b | 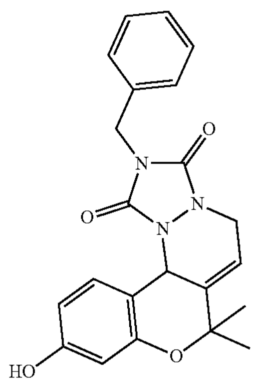 [SMILES: CC1(C)Oc2cc(O)ccc2C2C1=CCn1c(=O)n(Cc3ccccc3)c(=O)n12] | 391.43 | 391.01 [M]⁺ | $^1$H-NMR (500 MHz, CDCl$_3$): δ 7.48 (d, J = 8.0 Hz, 2H), 7.37-7.30 (m, 3H), 6.68 (d, J = 8.5 Hz, 1H), 6.38 (d, J = 2.0 Hz, 1H), 6.34 (dd, J = 8.5 and 2.0 Hz, 1H), 5.74 (t, J = 2.5 Hz, 1H), 5.56 (s, 1H), 4.82 (d, J = 4.5 Hz, 2H), 4.19 (dd, J = 16.5 and 5.0 Hz, 1H), 3.95 (dt, J = 16.5 and 2.5 Hz, 1H), 1.55 (s, 3H), 1.54 (s, 3H), 1.23 (q, J = 7.5 Hz, 3H), 1.10 (d, J = 7.5 Hz, 18H). |
| 2c | 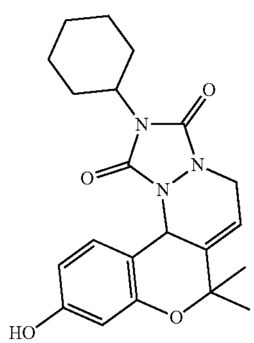 [SMILES: CC1(C)Oc2cc(O)ccc2C2C1=CCn1c(=O)n(C3CCCCC3)c(=O)n12] | 383.45 | 384.01 | $^1$H-NMR (500 MHz, CDCl$_3$): δ 6.75 (d, J = 8.5 Hz, 1H), 6.45 (dd, J = 8.5 and 2.5 Hz, 1H), 6.40 (d, J = 2.0 Hz, 1H), 5.73 (t, J = 2.5 Hz, 1H), 5.55 (s, 1H), 4.15 (dd, J = 16.0 and 5.0 Hz, 1H), 4.02 (tt, J = 10.0 and 3.0 Hz, 1H), 3.92 (dt, J = 16.0 and 2.5 Hz, 1H), 2.23 (t, J = 2.5 Hz, 2H), 1.90-1.83 (m, 6H), 1.71-1.67 (m, 2H), 1.56 (s, 3H), 1.53 (s, 3H), 1.23 (q, J = 7.5 Hz, 3H), 1.08 (d, J = 7.5 Hz, 18H). |
| 2d | 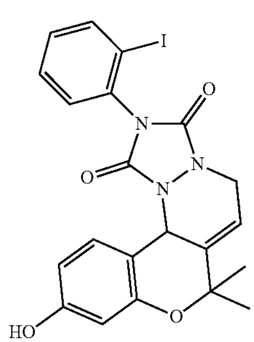 [SMILES: CC1(C)Oc2cc(O)ccc2C2C1=CCn1c(=O)n(-c3ccccc3I)c(=O)n12] | 503.30 | 503.86 | $^1$H-NMR (500 MHz, CDCl$_3$): δ 8.02 (t, J = 8.0 Hz, 1H), 7.52 (d, J = 7.5 Hz, 1H), 7.42 (d, J = 7.5 Hz, 1H), 7.36 (t, J = 7.5 Hz, 1H), 6.97 (d, J = 8.5 Hz, 1H), 6.49 (dd, J = 8.5 and 2.0 Hz, 1H), 6.44 (d, J = 2.0 Hz, 1H), 5.83 (t, J = 2.5 Hz, 1H), 5.73 (s, 1H), 4.32 (dd, J = 16.5 and 5.0 Hz, 1H), 4.12 (dt, J = 16.5 and 2.5 Hz, 1H), 1.61 (s, 3H), 1.60 (s, 3H), 1.23 (q, J = 7.5 Hz, 3H), 1.08 (d, J = 7.5 Hz, 18H) |

TABLE 2-continued

| Compound | Structure | Molecular Weight | MS Analysis Value (Molecular Weight +H⁺) | NMR |
|---|---|---|---|---|
| 2e | 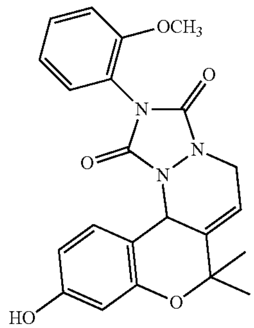 [SMILES: COc1ccccc1-n1c(=O)n2n(c1=O)C1C(=CC2)C(C)(C)Oc2cc(O)ccc21] | 407.43 | 408.2 | ¹H NMR (400 MHz, DMSO-d$_6$) δ 9.47 (s, 1H), 7.53 (t, J = 7.8 Hz, 1H), 7.41 (d, J = 8.0 Hz, 1H), 7.26 (d, J = 8.8 Hz, 1H), 7.11 (t, J = 7.6 Hz, 1H), 6.91 (d, J = 8.4 Hz, 1H), 6.38-6.42 (m, 1H), 6.27 (s, 1H), 5.93 (s, 1H), 5.58 (s, 1H), 4.02-4.24 (m, 2H), 3.88 (s, 3H), 1.55 (s, 3H), 1.51 (s, 3H) (more stable conformer); ¹³C NMR (100 MHz, DMSO-d$_6$) δ 158.2, 158.2, 155.4, 154.0, 153.9, 151.4, 136.5, 131.2, 130.4, 123.7, 120.7, 119.4, 114.8, 112.5, 104.3, 104.2, 79.2, 56.0, 49.3, 44.1, 27.3, 26.8 |
| 2f | 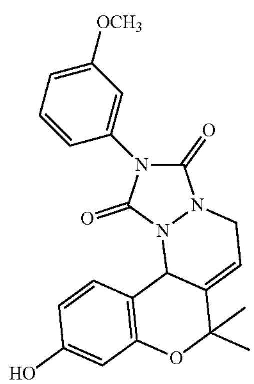 [SMILES: COc1cccc(-n2c(=O)n3n(c2=O)C2C(=CC3)C(C)(C)Oc3cc(O)ccc32)c1] | 407.43 | 407.98 | ¹H-NMR (500 MHz, CDCl$_3$): δ 7.43 (t, J = 8.0 Hz, 1H), 7.24 (d, J = 9.0 Hz, 1H), 7.20 (t, J = 2.0 Hz, 1H), 6.97 (dd, J = 8.5 and 2.5 Hz, 1H), 6.93 (d, J = 8.5 Hz, 1H), 6.48 (dd, J = 8.5 and 2.5 Hz, 1H), 6.44 (d, J = 2.0 Hz, 1H), 5.81 (t, J = 2.5 Hz, 1H), 5.70 (s, 1H), 4.31 (dd, J = 16.5 and 5.0 Hz, 1H), 4.10 (dt, J = 16.5 and 2.5 Hz, 1H), 3.87 (s, 3H), 1.60 (s, 3H), 1.59 (s, 3H), 1.23 (q, J = 7.5 Hz, 3H), 1.08 (d, J = 7.5 Hz, 18H) |
| 2g | 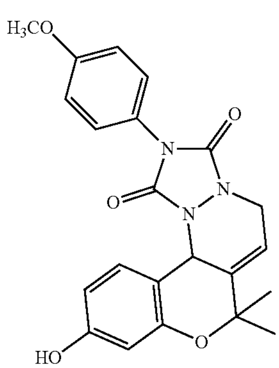 [SMILES: COc1ccc(-n2c(=O)n3n(c2=O)C2C(=CC3)C(C)(C)Oc3cc(O)ccc32)cc1] | 407.43 | 407.92 | ¹H-NMR (500 MHz, CDCl$_3$): δ 7.51 (d, J = 10.0 Hz, 2H), 7.03 (d, J = 10.0 Hz, 2H), 6.91 (d, J = 8.0 Hz, 1H), 6.47 (dd, J = 8.5 and 2.0 Hz, 1H), 6.42 (d, J = 2.5 Hz, 1H), 5.80 (t, J = 2.5 Hz, 1H), 5.68 (s, 1H), 4.30 (dd, J = 16.5 and 5.0 Hz, 1H), 4.08 (dt, J = 16.5 and 2.5 Hz, 1H), 3.85 (s, 3H), 1.58 (s, 3H), 1.57 (s, 3H), 1.23 (q, J = 7.5 Hz, 3H), 1.08 (d, J = 7.5 Hz, 18H). |

TABLE 2-continued

| Compound | Structure | Molecular Weight | MS Analysis Value (Molecular Weight +H⁺) | NMR |
|---|---|---|---|---|
| 2h | 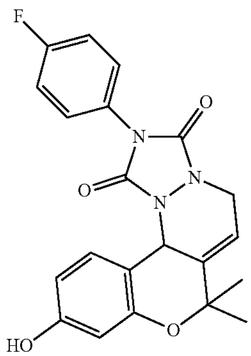 [SMILES: CC1(C)Oc2cc(O)ccc2C2C1=CCn1c(=O)n(-c3ccc(F)cc3)c(=O)n12] | 395.39 | 393.82 [M − H]⁻ | ¹H-NMR (500 MHz, CDCl₃): δ 7.62 (dt, J = 7.0 and 2.5 Hz, 2H), 7.20 (t, J = 8.5 Hz, 2H), 6.90 (d, J = 8.5 Hz, 1H), 6.47 (dd, J = 8.5 and 2.0 Hz, 1H), 6.43 (d, J = 2.0 Hz, 1H), 5.80 (t, J = 2.5 Hz, 1H), 5.68 (s, 1H), 4.29 (dd, J = 16.5 and 5.0 Hz, 1H), 4.09 (dt, J = 16.5 and 2.5 Hz, 1H), 1.59 (s, 3H), 1.57 (s, 3H), 1.23 (q, J = 7.5 Hz, 3H), 1.08 (d, J = 7.5 Hz, 18H); ¹³C-NMR (125 MHz, CDCl₃): δ 163.2, 161.2, 157.4, 154.2, 153.9, 151.6, 137.9, 127.6(d), 124.3, 116.6, 116.4, 113.6, 112.7, 109.6, 79.1, 50.5, 44.4, 27.9, 27.1, 18.1, 12.8. |
| 2i | 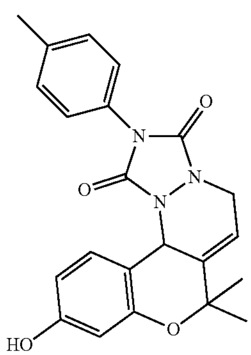 | 391.43 | 391.1535 [M]⁺ | ¹H-NMR (500 MHz, CDCl₃): δ 7.46 (d, J = 8.5 Hz, 2H), 7.31 (d, J = 8.5 Hz, 2H), 6.90 (d, J = 8.5 Hz, 1H), 6.36 (dd, J = 8.5 and 2.5 Hz, 1H), 6.33 (d, J = 2.5 Hz, 1H), 5.81 (t, J = 2.5 Hz, 1H), 5.68 (s, 1H), 5.44 (br.s, 1H), 4.29 (dd, J = 16.5 and 5.0 Hz, 1H), 4.08 (dt, J = 16.5 and 2.5 Hz, 1H), 2.40 (s, 3H), 1.57 (s, 6H), ¹³C-NMR (125 MHz, CDCl₃): δ 157.3 154.2, 154.1, 151.8, 138.8 137.4, 130.0, 128.3, 125.7, 124.5, 115.3, 112.6, 109.1, 105.0, 78.9, 50.2, 44.3, 27.6, 26.8, 21.3 |
| 2j | 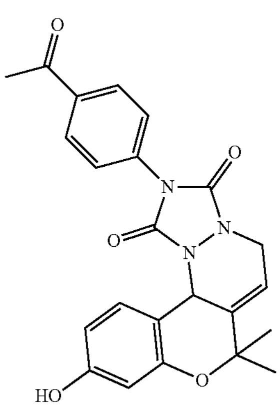 [SMILES: CC(=O)c1ccc(-n2c(=O)n3n(c2=O)C2C(=CC3)C(C)(C)Oc3cc(O)ccc32)cc1] | 419.44 | 420.1 | ¹H NMR (400 MHz, DMSO-d₆) δ 9.47 (s, 1H), 8.13 (d, J = 8.0 Hz, 2H), 7.79 (d, J = 8.8 Hz, 2H), 6.87 (d, J = 8.4 Hz, 1H), 6.37 (dd, J = 8.8 Hz, 2.0 Hz, 1H), 6.25 (d, J = 1.6 Hz, 1H), 5.95 (s, 1H), 5.61 (s, 1H), 4.11-4.25 (m, 2H), 2.64 (s, 3H), 1.54 (s, 3H), 1.51 (s, 3H); ¹³C NMR (100 MHz, DMSO-d₆) δ 197.2, 158.2, 153.8, 153.3, 150.5, 136.0, 135.8, 135.6, 128.9, 125.7, 124.5, 114.6, 113.6, 108.6, 104.1, 79.0, 49.3, 44.0, 27.4, 26.9, 26.8 |

TABLE 2-continued

| Compound | Structure | Molecular Weight | MS Analysis Value (Molecular Weight +H⁺) | NMR |
|---|---|---|---|---|
| 2k | 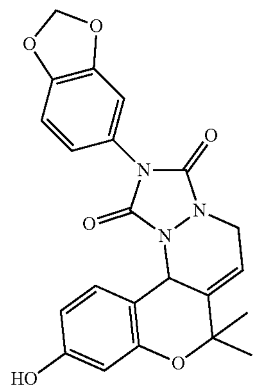 [SMILES: CC1(C)Oc2cc(O)ccc2C2C1=CCn1c(=O)n(-c3ccc4c(c3)OCO4)c(=O)n12] | 421.41 | 422.1 | ¹H NMR (400 MHz, CDCl₃) δ 7.00-7.04 (m, 2H), 6.83-6.92 (m, 2H), 6.31-6.36 (m, 2H), 6.07 (s, 1H), 6.02 (s, 2H), 5.78-5.81 (m, 1H), 5.66 (s, 1H), 4.24-4.30 (m, 1H), 4.04-4.10 (m, 1H), 1.78 (s, 6H); ¹³C NMR (100 MHz, CDCl₃) δ 157.2, 154.3, 154.1, 151.8, 148.3, 147.9, 137.4, 124.6, 124.4, 120.1, 115.4, 112.7, 109.0, 108.6, 107.4, 105.0, 102.0, 78.9, 50.2, 44.3, 27.6, 26.9 |
| 2l | 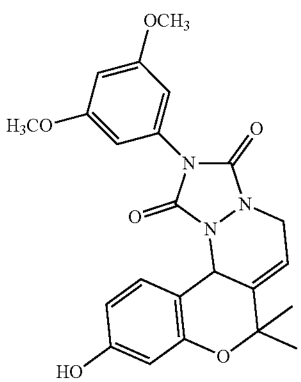 [SMILES: COc1cc(OC)cc(-n2c(=O)n3n(c2=O)C2C(=CC3)C(C)(C)Oc3cc(O)ccc32)c1] | 437.45 | 438.1 | ¹H NMR (400 MHz, DMSO-d₆) δ 9.46 (s, 1H), 6.84 (d, J = 8.4 Hz, 1H), 6.77 (d, J = 2.4 Hz, 2H), 6.614 (s, 1H), 6.38 (dd, J = 8.0 Hz, 2.2 Hz, 1H), 6.25 (d, J = 2.4 Hz, 1H), 5.94 (s, 1H), 5.57 (s, 1H), 4.07-4.22 (m, 2H), 3.79 (s, 6H), 1.53 (s, 3H), 1.50 (s, 3H); ¹³C NMR (100 MHz, DMSO-d₆) δ 160.4, 158.2, 153.8, 153.7, 150.8, 136.1, 133.0, 124.4, 114.6, 113.6, 108.6, 105.0, 79.0, 55.6, 55.5, 49.2, 44.0, 27.3, 26.7 |
| 2m | 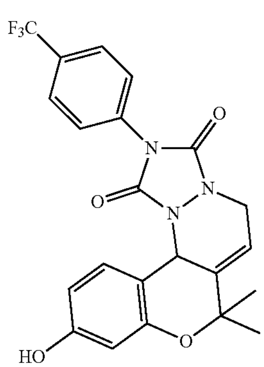 [SMILES: CC1(C)Oc2cc(O)ccc2C2C1=CCn1c(=O)n(-c3ccc(C(F)(F)F)cc3)c(=O)n12] | 445.12 | 446.0 | ¹H NMR (400 MHz, DMSO-d₆) δ 9.47 (brs, 1H), 7.95 (d, J = 8.4 Hz, 2H), 7.89 (d, J = 8.8 Hz, 2H), 6.88 (d, J = 8.8 Hz, 1H), 6.37 (dd, J = 8.4 Hz, 1.6 Hz, 1H), 6.25 (d, J = 2.0 Hz, 1H), 5.95 (s, 1H), 5.61 (s, 1H), 4.16-4.23 (m, 2H), 1.54 (s, 3H), 1.51 (s, 3H); ¹³C NMR (100 MHz, DMSO-d₆) δ 158.2, 153.8, 153.2, 150.4, 130.9, 135.2, 126.4, 126.1, 124.5, 114.5, 113.5, 108.6, 104.1, 79.2, 79.0, 49.3, 44.0, 27.4, 26.8 |

TABLE 2-continued

| Compound | Structure | Molecular Weight | MS Analysis Value (Molecular Weight +H$^+$) | NMR |
|---|---|---|---|---|
| 2n | 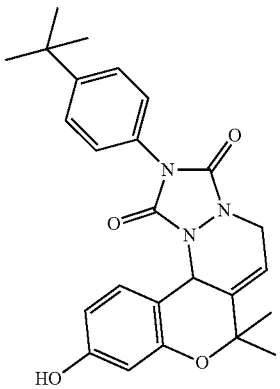 [SMILES: CC1(C)Oc2cc(O)ccc2C2C1=CCn1c(=O)n(-c3ccc(C(C)(C)C)cc3)c(=O)n12] | 433.51 | 433.96 | $^1$H-NMR (500 MHz, CDCl$_3$): δ 7.53 (s, 4H), 6.91 (d, J = 8.5 Hz, 1H), 6.46 (dd, J = 8.5 and 2.5 Hz, 1H), 6.42 (d, J = 2.5 Hz, 1H), 5.80 (t, J = 2.5 Hz, 1H), 5.69 (s, 1H), 4.31 (dd, J = 16.5 and 5.0 Hz, 1H), 4.08 (dt, J = 16.5 and 2.5 Hz, 1H), 1.59 (s, 3H), 1.57 (s, 3H), 1.35 (s, 9H), 1.23 (q, J = 7.5 Hz, 3H), 1.08 (d, J = 7.5 Hz, 18H); $^{13}$C-NMR (125 MHz, CDCl$_3$): δ 157.3, 154.2, 151.9, 151.6, 147.9, 128.7, 126.5, 125.3, 124.4, 116.5, 113.6, 112.8, 109.6, 79.1, 50.5, 44.5, 35.0, 31.5, 29.9, 27.9, 27.1, 18.1, 12.9 |
| 2o | 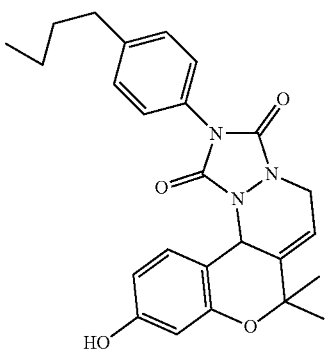 [SMILES: CCCCc1ccc(-n2c(=O)n3n(c2=O)C2C(=CC3)C(C)(C)Oc3cc(O)ccc32)cc1] | 433.51 | 434.2 | $^1$H NMR (400 MHz, CDCl$_3$) δ 7.48 (d, J = 8.0 Hz, 2H), 7.31 (d, J = 8.4 Hz, 2H), 6.88 (d, J = 8.0 Hz, 1H), 6.32-6.37 (m, 2H), 5.78-5.81 (m, 2H), 5.68 (s, 1H), 4.28 (dd, J = 16.4 Hz, 4.4 Hz, 1H), 4.05-4.10 (m, 1H), 2.65 (t, J = 7.6 Hz, 2H), 1.55-1.64 (m, 2H), 1.56 (s, 6H), 1.37 (sextet, J = 7.5 Hz, 2H), 0.94 (t, J = 7.2 Hz, 2H); $^{13}$C NMR (100 MHz, CDCl$_3$) δ 157.1, 154.3, 154.1, 151.8, 143.6, 137.5, 129.4, 128.6, 125.5, 124.7, 115.6, 112.8, 109.0, 105.0, 79.0, 50.2, 44.3, 35.5, 33.6, 27.6, 26.9, 22.4, 14.1 |

Test Example 1: Inflammation Inhibiting Effect of Compound 1d on the CLP Mouse Model When pathogens invade a host organism, an acute inflammatory response is initiated in the body. Macrophages, one of the key immune cells that mediate the inflammatory responses, are activated following their recognition of pathogens, which subsequently induces the secretion of various pro-inflammatory cytokines including HMGBs, TNF-α, and IL-6.

As shown in FIG. 1, after activation of macrophage upon recognition of LPS (Lipopolysaccharides), HMGBs are translocated from nucleus to cytosol and subsequently released to the extracellular milieu.

These pro-inflammatory cytokines activate other adjacent macrophages and initiate a positive feedback mechanism of immune response.

On the other hand, when Compound 1d is treated, it can be seen that the inhibited immune response is exhibited.

Figure 2:
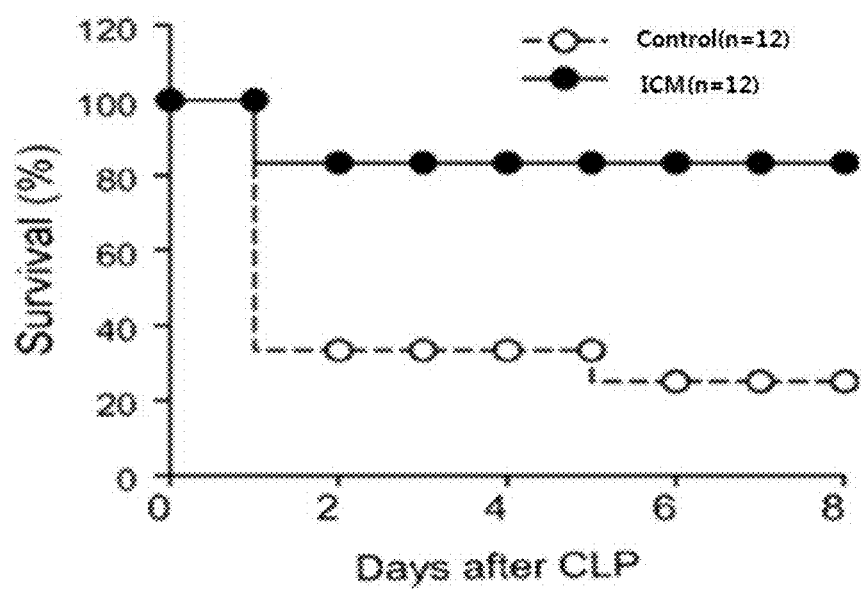
FIG. 2 shows the survival rate of vehicle- and Compound 1d-trated CLP mouse model.

FIG. 2 shows the survival rate of the CLP-induced mice after the intraperitoneal (ip) injection in the CLP-induced mice of 10 mg/kg of Compound 1d for 9 days.

As shown in FIG. 2, the survival rate of the CLP-induced mice significantly increased when compared with that of the vehicle-treated group.

Figure 3:
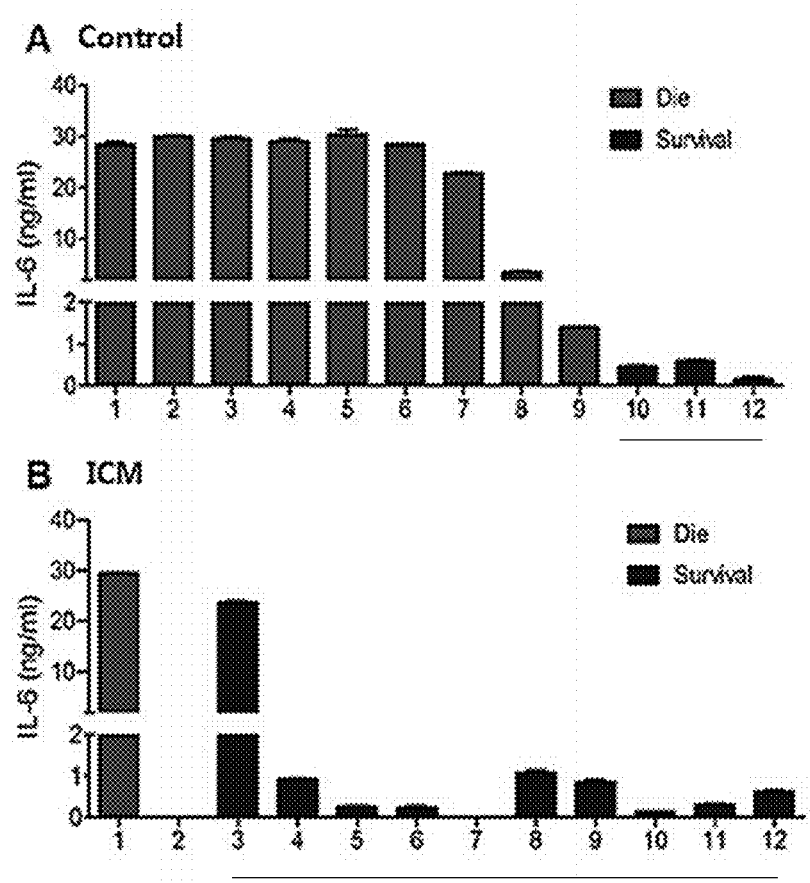
FIG. 3 shows the IL-6 levels of vehicle- (A) and Compound 1d-trated CLP mouse model (B).

In addition, the survival rate and IL-6 levels after administration of Compound 1d at a daily dose of 10 mg/kg for 9 days starting from 1 hour before CLP induction in the CLP mouse model are shown in FIG. 3.

As shown in FIG. 3, IL-6 levels in surviving mice were significantly reduced in the Compound 1d-treated group as compared with the control group.

In conclusion, IL-6 levels are highly correlated with the survival rates.

Test Example 2: Inflammation Inhibiting Effect of Compounds 1a to 1j

When inflammation is induced, the secretion of nitric oxide is increased, and the treatment of inflammation inhibitor inhibits nitric oxide secretion.

Thus, the Griess assay was used to measure nitric oxide secretion for inflammation inhibition in Raw264.7 cells.

Raw264.7 Cell Culture

Raw 264.7 macrophage cell was cultured in Dulbecco Modified Eagle Medium (DMEM) with 10% (v/v) fetal bovine serum (FBS) and 1% (v/v) antibiotic-anti mycotic solution.

Cell was maintained in a 100 mm cell culture dish under cell culture conditions (5% CO2 incubator at 37° C. with humidified atmosphere).

Griess Assay

Griess assay reagent was generated prior to the assay with the following contents listed below: N-(1-naphthyl) ethylenediamine dihydrochloride, 0.1% (m/v); sulfanilamide, 1% (m/v); phosphoric acid (85%); 5% (v/v) in deionized water.

Raw 264.7 cell was seeded in transparent 96-well plate and maintained for 1 day. Media was aspirated, and each well was washed with serum free DMEM for twice. Each well was refilled with serum-free DMEM.

Then 100 ng/mL LPS and compounds were treated afterward and cultured for 24 hours. After the incubation, the supernatant culture media was transferred to new 96-well plate and mixed with 50 μL of Griess assay reagent.

Media-reagent mixture was incubated at room temperature for several minutes. Absorbance was read at 548 nm. Four wells each were used for the control experiment, LPS and DMSO (without any compounds) treated well, and DMSO-only treated well. Blank values were measured.

Blank values were measured by mixing 50 μL of Griess assay reagent with 10% PBS and 1% antibiotic-antimycotic containing DMEM. All experiments were independently performed at least three times.

When the compounds 1a to 1j were each treated, the inhibition rate (%) of nitric oxide release was confirmed as compared with the control group, and the results are shown in Table 3 below.

Compounds 1a to 1h, in which the substituents $R_1$ to $R_3$ of the benzopyran core structure are modified, have the lower inhibitory effect on the NO release, as compared to Compound 1d, which has an inhibition rate against NO release of 87%.

In addition, when the methyl group at $R_4$ position in Compound 1d was modified as in Compound 1i and 1j, the inhibitory effect of NO release was significantly reduced.

Thus, these results indicate that the substituents R1-R4 in Compound 1d are the most appropriate for the anti-inflammatory effects.

Figure 4:
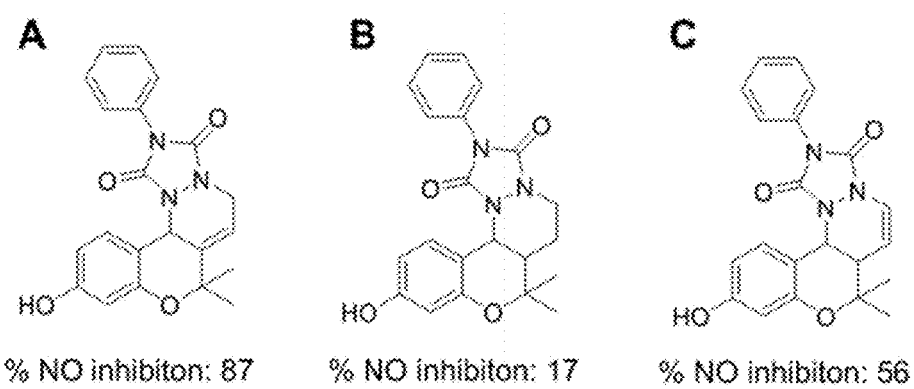
FIG. 4 shows the inhibition rate of No release in Compound 1d (A), the compounds which the double bond of the tetrahydropyridazine ring is moved (B) or eliminated (C).

Test Example 3: Inflammation Inhibitory Effect of the Compounds in which a Double Bond of a Tetrahydropyridazine Ring is Moved or Removed As for the compounds in which the double bond of the tetrahydropyridazine ring in Compound 1d is moved or eliminated, the inhibition rate of NO release was measured in the same manner as in Test Example 2. The above results are shown in FIG. 4.

It was measured that the compound in which the double bond is moved (B, 56%) or eliminated (C, 17%) reduced the inhibition rate of NO release, compared with that of Compound 1d (A, 87%).

Therefore, it is confirmed that the inhibitory effect of NO release due to the migration or elimination of the double bond was rather reduced.

Test Example 4: Inflammation Inhibitory Effect of Compound 2a to 2o (Inhibition Rate of NO Release)

The inhibition rate of NO release for Compounds 2a to 2o prepared in Example 2 was tested in order to confirm the

TABLE 3

| Compound | R1 | R2 | R3 | R4 | NO Inhibition rate (%) |
|---|---|---|---|---|---|
| 1a | H | H | H | methyl | 83 |
| 1b | H | N-methylamino | H | Methyl | 52 |
| 1c | H | Fluoro | H | Methyl | 79 |
| 1d | H | hydroxy | H | Methyl | 87 |
| 1e | H | methoxy | H | Methyl | 44 |
| 1f | methoxy | H | H | Methyl | 55 |
| 1g | methoxy | methoxy | H | Methyl | 44 |
| 1h | H | Methoxy | hydroxy | methyl | 26 |
| 1i | H | hydroxy | H | 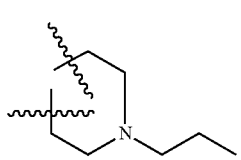 [SMILES: *CCN(CC*)CCC] | 47 |
| 1j | H | hydroxy | H |  | 36 |

As shown in Table 3, Compound 1d inhibited the NO release by 87% in Raw264.7 cells compared to the vehicle.

anti-inflammatory effect for the above compounds. The experimental results are shown in Table 4.

TABLE 4

| Compound | Structure | NO Inhibition Rate (%) |
|---|---|---|
| 1d | [structure: N-phenyl triazolidinedione fused chromene with HO and gem-dimethyl] | 87 |
| 2a | [structure: N-methyl (H₃C) analog] | 45 |
| 2b | [structure: N-benzyl analog] | 70 |
| 2c | [structure: N-cyclohexyl analog] | 63 |

TABLE 4-continued

| Compound | Structure | NO Inhibition Rate (%) |
|---|---|---|
| 2d | [structure: N-(2-iodophenyl) analog] | 48 |
| 2e | [structure: N-(2-methoxyphenyl) analog] | 66 |
| 2f | [structure: N-(3-methoxyphenyl) analog] | 96 |
| 2g | [structure: N-(4-methoxyphenyl) analog] | 89 |

TABLE 4-continued

| Compound | Structure | NO Inhibition Rate (%) |
|---|---|---|
| 2h | (4-fluorophenyl derivative) | 87 |
| 2i | (4-methylphenyl derivative) | 94 |
| 2j | (4-acetylphenyl derivative) | 93 |
| 2k | (benzo[1,3]dioxol-5-yl derivative) | 92 |
| 2l | (3,5-dimethoxyphenyl derivative) | 94 |
| 2m | (4-trifluoromethylphenyl derivative) | 85 |
| 2n | (4-tert-butylphenyl derivative) | 99 |
| 2o | (4-butylphenyl derivative) | 99 |

As shown in Table 4, various substituents at the ortho, meta, and para positions of the original phenyl ring were incorporated. The ortho-substituted compounds 2d (63%) and 2e (48%) did not improve the inhibitory effects on NO release, when compared with that of Compound 1d.

In contrast, the compound having a methoxy group at the meta position, Compound 2f (96%), and the compound having a methoxy group at para position, Compound 2g (89%) positions enhanced the inhibitory effects on NO release when compared with that of Compound 1d (87%).

As a result, it is confirmed that Compounds 2f, 2g to 2l, 2n and 2o are superior to Compound 1d in terms of the inhibitory effect of NO release.

Test Example 5: Relative Cell Viability of Compound 2a to 2o

Relative cell viability of Compound 2a to 2o prepared in Examples 2 was measured by WST (water-soluble tetrazolium) analysis.

WST (Water-Soluble Tetrazolium) Analysis

Raw 264.7 cell was seeded in transparent 96-well plate and maintained for 1 day.

Media was aspirated, and each well was washed with serum free DMEM for twice. Each well was refilled with serum-free DMEM. Then, 100 ng/mL LPS and compounds were treated afterward and cultured for 24 hours. After the incubation, the supernatant culture media was transferred to new 96-well plate.

Immediately after transferring media, cell-seeded wells were refilled with 100 µL of 10% FBS and 1% antibiotic-antimycotic containing DMEM. Then, 10 µL of Ez-cytox WST assay reagent was used to treat each well, following the manufacturer's protocol.

After incubating for 20 min in a 5% CO2 incubator at 37° C. with humidified atmosphere, absorbance was read at 450 nm.

Blank values were obtained from the well only treated with 10% FBS and 1% antibiotic-antimycotic containing DMEM. All experiments were independently performed at least three times. The results of relative cell viability are shown in Table 5.

TABLE 5

| Compound | Relative Cell Viability (%) |
| --- | --- |
| 1d | 105 |
| 2a | 114 |
| 2b | 106 |
| 2c | 117 |
| 2d | 109 |
| 2e | 115 |
| 2f | 118 |
| 2g | 127 |
| 2h | 109 |
| 2i | 130 |
| 2j | 111 |
| 2k | 121 |
| 2l | 121 |
| 2m | 106 |
| 2n | 105 |
| 2o | 50 |

As shown in Table 5, the relative cell activity of Compound 1d was 105. Compounds 2a to 2l showed superior relative cell activity as compared with Compound 1d.

Test Example 6: Inflammation Inhibitory Effect of Compound 2a to 2l (TNF-α Secretion Inhibition Rate)

From the results of test example 5, Compounds 2m to 2o showed similar or inferior relative cell viability, compared with that of Compound 1d, and thus were not tested in text example 6.

From the results of test example 4, Compounds 2a to 2e showed similar or inferior the inhibitory effect of NO release, compared with that of Compound 1d, and thus were not tested in text example 6.

Thus, in order to additionally confirm the inflammation inhibitory effects of Compounds 2f to 2l, the inhibition rate of TNF-α secretion was quantitatively measured by ELISA.

Cells were treated with each Compound 1d, or 2f to 2l, and LPS for 24 hours, followed by ELISA for TNF-α present in the culture solution.

ELISA

In order to measure the amount of secreted TNF-α, Raw264.7 cell was seeded in transparent 96-well plate and maintained for 1 day. Media was aspirated after 1 day and replaced to serum-free DMEM with 1% (v/v) antibiotic-antimycotic solution. LPS and compounds were treated in a final concentration of 100 ng/mL and 10 µM.

After 4 hours, media were transferred to new transparent 96-well plate and diluted with 1% BSA in PBS solution. ELISA assay was performed following the manufacturer's protocol. For the quantification of serum IL-6 level in CLP-induced C57BL/6 mice, blood was collected from mice at 24 hours after surgery.

ELISA plates (Costar, Cambridge, Mass.) were coated overnight with anti-IL-6 monoclonal antibody (eBioscience, San Diego, Calif.) at 4° C. Wells were blocked with PBS containing 1% bovine serum albumin (Sigma-Aldrich, St. Louis, Mo.) for 1 hour at room temperature (RT) and incubated with serum overnight at 4° C.

After washing, plates were incubated with biotinylated anti-IL-6 antibody (eBioscience) for 1 hour at RT. Streptavidin-conjugated horseradish peroxidase (eBioscience) is attached for 1 hour at RT. Then, Color was developed using TMB solution (eBioscience), Absorbance was read at 450 nm with a Multiskan Ascent (Labsystems, Kennett Square, Pa.). All experiments were independently performed at least three times.

Standard curve was plotted by the dose-dependent treatment of the control TNF-α protein provided with the ELISA kit. Blank value was measured by adding solutions without TNF-α substrate.

The TNF-α secretion inhibition rate of Compounds 1d, and 2f to 2l was confirmed, when compared with control groups. The experimental results are shown in Table 6.

TABLE 6

| Compound | TNF-α Inhibition Rate (%) |
| --- | --- |
| 1d | 43 |
| 2f | 38 |
| 2g | 44 |
| 2h | 44 |
| 2i | 45 |
| 2j | 68 |
| 2k | 46 |
| 2l | 60 |

As show in Table 6, Compound 1d, and 2f to 2l, were found to inhibit TNF-α release in Raw 264.7 cells. Especially, when compared with Compound 1d (43%), Compounds 2j (68%) and 2l (60%) show superior TNF-α release inhibitory effect.

Test Example 7: Inhibition of HMGB1 Release

From the results shown in Table 6, Compounds 2j (68%) and 2l (60%) had better TNF-α release inhibitory effect than that of Compound 1d (43%). Therefore, it was analyzed with the immunofluorescence whether Compounds 2j and 2l may inhibit the cellular localization of HMGB1 upon LPS treatment.

Immunofluorescence

Raw264.7 cell was seeded in "Nunc Lab-Tek II" chambered coverglass and maintained for 1 day.

Then, 20 μM of compounds were treated 1 hour prior to 500 ng/mL LPS treatment for 2 hours.

After aspirating the media and washing with PBS, 200 μl of 4% paraformaldehyde solution was treated and incubated at room temperature for 20 minutes. Then, 4% paraformaldehyde solution was aspirated and the sample was washed with PBS three times.

For the permeabilization to enable antibody binding, 200 μL of methanol was treated and incubated at −20° C. for 20 minutes. Methanol was then removed and the sample was washed with PBS three times.

Sample was blocked with 2% BSA in PBS solution at room temperature for 1 hour. Then, 2% BSA in PBS solution was removed and primary antibody containing 1% BSA in PBS was treated at 4° C. overnight. Antibody concentration was optimized according to the manufacturer's protocol. Primary antibody solution was removed and the sample was washed with PBS three times. Secondary antibody containing 1% BSA in PBS solution was treated at room temperature for 1 hour.

The secondary antibody used was goat anti rabbit TRITC labeled antibody from Abcam.

After 1 hour, antibody solution was aspirated and the sample was washed with PBS three times. For nucleus staining, Hoechst 33342 was diluted in PBS, and each well was treated and incubated at room temperature for 1 hour. Hoechst 33342 was then removed and the chamber was filled with PBS, continued for imaging using DeltaVision microscope.

Figure 5:
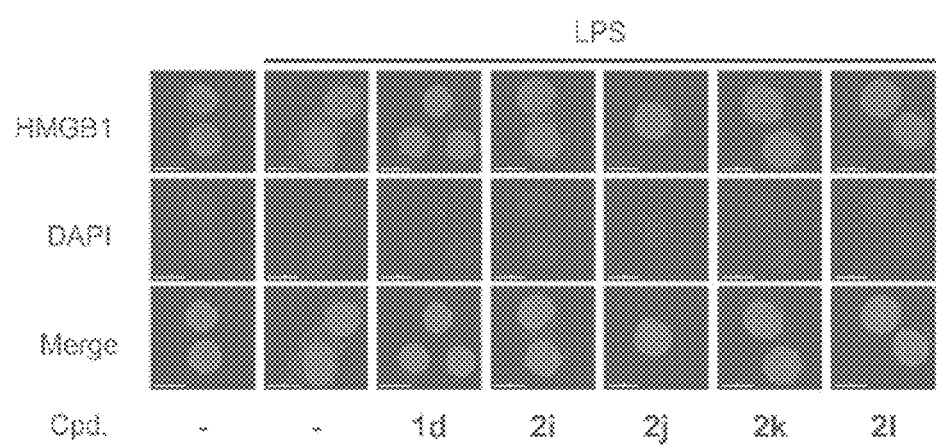
FIG. 5 shows the cellular immunofluorescence images of HMGB1, after the pretreatment of Compounds 1d, and 2i to 2l.

The results of the above analysis are shown in FIG. 5. Compounds 1d, and 2j to 2l inhibited the translocation of HMGB1 from the nucleus to the cytosol.

Test Example 8: Reduction of IL-6 Secretion

From the results shown in Table 6, Compounds 2j (68%) and 2l (60%) had better TNF-α release inhibitory effect than that of Compound 1d (43%). Therefore, the inhibitory effect of IL-6 release secretion was analyzed with the Western blot analysis in order to additionally confirm the inflammation inhibitory effect of Compounds 2j and 2l.

Western Blot Analysis Protein sampling was done in 4° C. Cells were harvested in RIPA lysis buffer containing protease inhibitor cocktail and phosphatase inhibitor.

After centrifugation at 15000 rpm for 20 minutes, supernatant was transferred to new 1.5 mL tube. Protein concentration was normalized with a Micro BCA protein assay kit. The protein samples were analyzed with the Western blot procedure. Protein was transferred into PVDF membrane after SDS-PAGE. Membrane was blocked after transfer step, with 2% BSA in TBST for 1 hour in room temperature.

Primary antibodies were treated overnight at 4° C. or 1 hour in room temperature, followed by washing with TBST.

HRP-conjugated secondary antibodies were treated for 1 hour in room temperature. Antibodies were diluted in 1% BSA in TBST solution, with the concentration indicated in antibody manufacturer's protocol. After washing with TBST, the membrane was developed by Amersham ECL prime solution. Chemiluminescent signal was measured by ChemiDoc MP imaging system, and relative quantification were followed using ImageLab 4.0 software. The quantification result was processed with GraphPad Prism 5.0 software.

Figure 6:
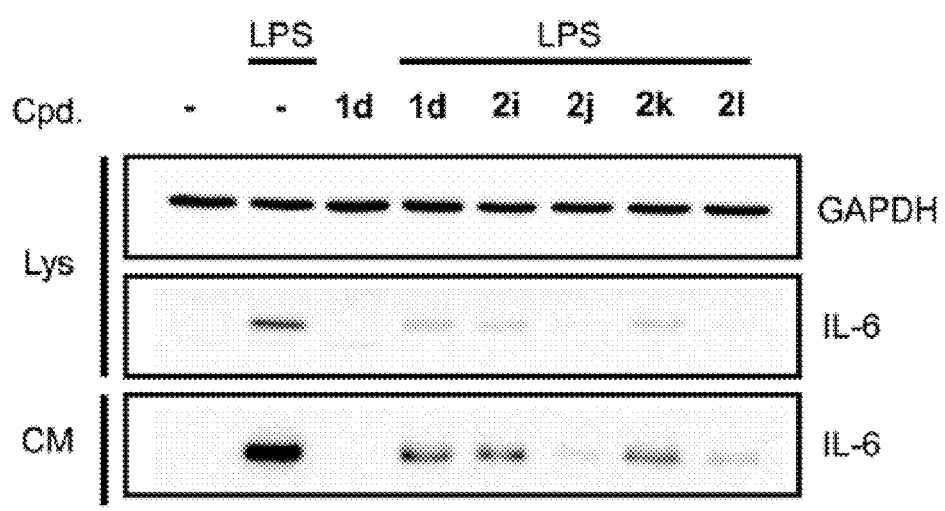
FIG. 6 shows the western blot analysis to confirm the inhibitory effect of IL-6 release, after the pretreatment of Compounds 1d, and 2i to 2l.

The result of the western blot is shown in FIG. 6. The level of IL-6 secreted from Raw 264.7 cells was significantly reduced when treated with Compounds 1d, and 2i to 2l. Especially, Compounds 2j and 2l showed superior inhibitory effect on IL-6 secretion.

Test Example 9: Relative Affinity for HMGB1

The binding energy of Compounds 1d, 2j and 2l as a ligand of HMCB1 was measured. The experimental results are shown in FIG. 7.

Figure 7:
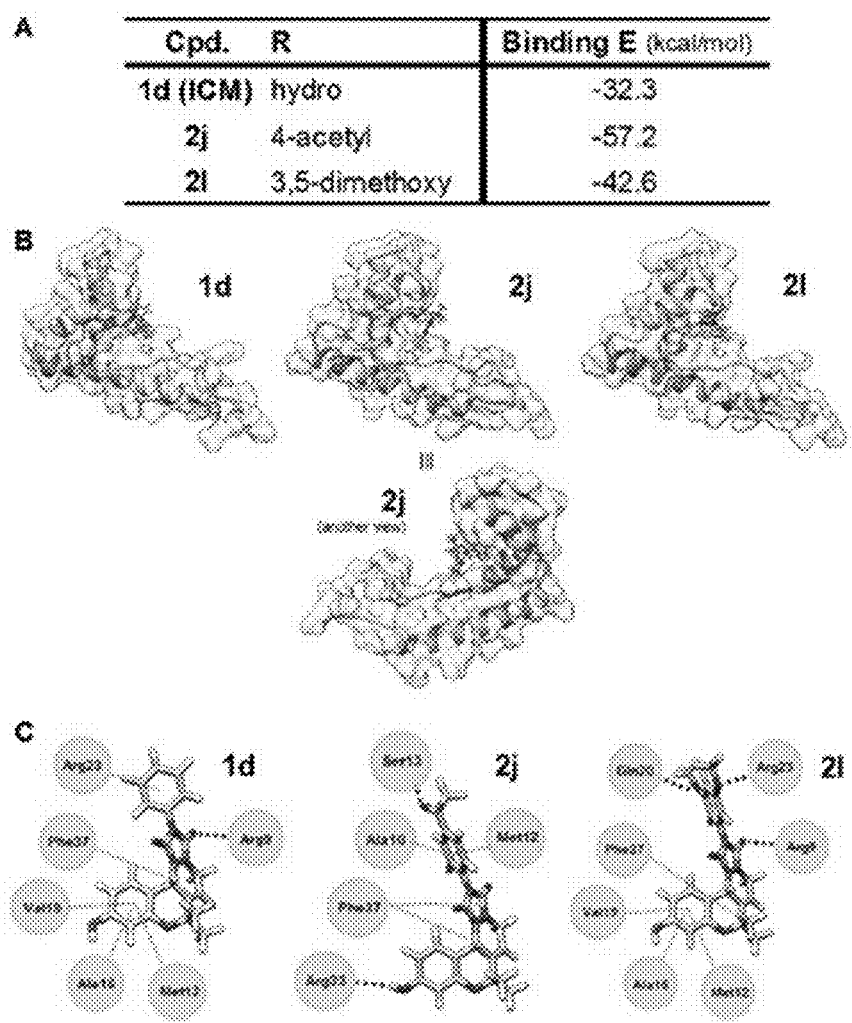
FIG. 7 shows the binding energy of Compounds 1d, 2j and 2l as a ligand of HMGB1 (A), binding mode (B) and interactive reaction of HMGB1 with adjacent amino acid.

As shown in FIG. 7, Compounds 2j and 2l were found to bind more tightly with HMGB1 than Compound 1d. Thus, it is confirmed that Compounds 2j and 2l have enhanced activities in the regulation of HMGB1.

Test Example 10: Inhibition of Inflammatory Signaling Pathway

Intracellular inflammatory signaling pathways play important roles in propagating immune responses in the activated macrophage.

Mitogen-activated protein kinase (MAPK) and nuclear factor kappa-light-chain enhancer in B cells (NF-κB) complex are two of the most important inflammatory signaling systems that regulate the release of HMGBs and other cytokines in macrophages.

There are three distinct types of MAPKs: p38 MAPK (p38), c-jun N-terminal kinases (JNKs), and extracellular signal-regulated kinase (ERK). Following the activation of macrophage, the MAPKs are phosphorylated and subsequently trigger the transduction of inflammatory signals within the cells.

Figure 8:
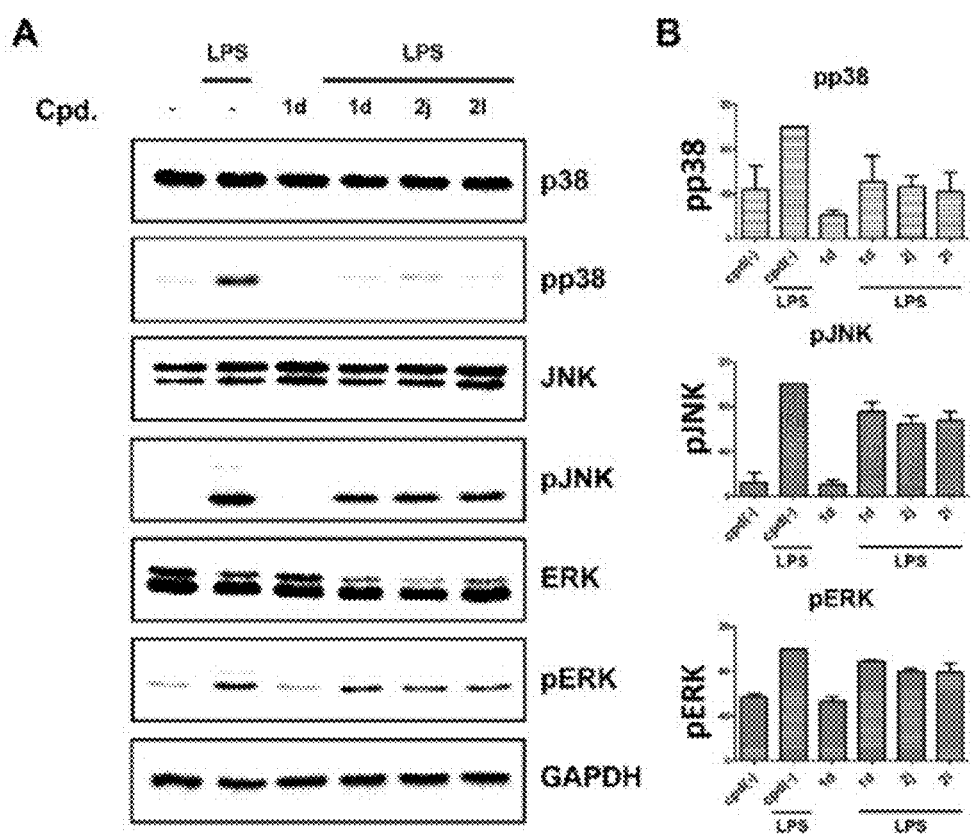
FIG. 8 shows the western blot analysis relative to the phosphorylation of p38 JNK, and ERK, after the pretreatment of Compounds 1d, and 2i to 2l in Raw264.7 cells (A), and the quantification of phosphorylation level of p38 JNK, and ERK, after the compounds by the western blot analysis.

The western blot data is shown in FIG. 8. It is confirmed that Compounds 1d, 2j and 2l clearly inhibited the phosphorylation of MAPK including p38, JNK, and ERK.

The NF-κB pathway is another key signaling pathway that regulates inflammatory responses. NF-κB is a complex of two different protein domains, p50 and p65. In the basal state, the activity of the NF-κB complex is inhibited by nuclear factor of kappa-light polypeptide gene enhancer in B-cells inhibitor (IκB).

When the activation signal reaches the macrophages, IκB kinase (IKK) phosphorylates IκB, which is subsequently degraded leading to the activation of the NF-κB complex. Then, the activated NF-κB translocates to the nucleus and acts as a transcription factor to produce pro-inflammatory cytokines. The migration of NF-κB to the nucleus plays an important role in the activation of macrophages in the inflammatory signaling pathway.

Figure 9:
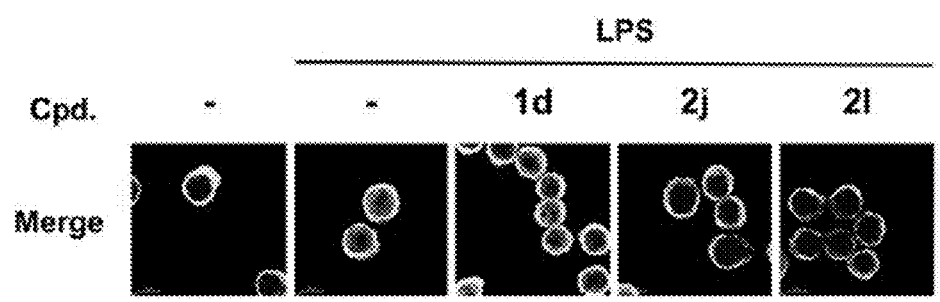
FIG. 9 shows the cellular NF-κB p65 immunofluorescence images after the pretreatment of Compounds 1d, 2j, and 2l in Raw264.7 cells, followed by 500 ng/mL LPS treatment.

As shown in FIG. 9, it is confirmed that Compounds 1d, 2j and 2l inhibit the migration of NF-κB to the nucleus. It is concluded that Compounds 1d, 2j, and 2l controlled and regulated the inflammatory signaling pathways in activated macrophages.

Test Example 11: Pharmacokinetics of Compounds

The aqueous solubility, liver microsomal stabilities and PK profiles was measure for Compounds 1d, 2j, and 2l in the in vivo CLP-induced mouse models. The experimental results are shown in Table 7.

TABLE 7

| compound | | 1d | 2j | 2l |
|---|---|---|---|---|
| solubility | Aqueous (μg/ml) | 23.5 ± 1.02 | 162.5 ± 2.12 | 65.1 ± 2.74 |
| microsomal stability | Mouse(%) | 0.41 ± 0.10 | 2.46 ± 1.83 | 20.2 ± 1.78 |
| | Human(%) | 0.82 ± 0.29 | 30.2 ± 2.81 | 41.2 ± 4.33 |
| PK data | $T_{max}$(h) | 0.14 ± 0.10 | 0.25 ± 0.00 | 0.14 ± 0.10 |
| | $C_{max}$(μg/ml) | 387 ± 122 | 100 ± 3.72 | 282 ± 87.0 |
| | AUC(μg/mL.h) | 327 ± 68.7 | 202 ± 28.1 | 218 ± 51.8 |
| | $T_{1/2}$(h) | 3.87 ± 0.84 | 3.45 ± 1.00 | 5.00 ± 0.98 |

Compounds 2j and 2l showed improved solubility in aqueous media and improved liver microsomal stability in both mice and humans, when compared with Compound 1d. In addition, Compounds 1d, 2j, and 2l were all easily administered by ip injection and maintained their activities for several hours.

Test Example 12: Effects on the CLP Mouse Model

The therapeutic effects of Compounds 1d, 2j, and 2l in CLP-induced mouse models were analyzed Compound 1d, 2j and 2l were administered intraperitoneally at a daily dose of 10 mg/kg for 21 days after the start of administration of CLP 1 hour before the induction. The survival rate was measured and is shown in FIG. 10.

Figure 10:
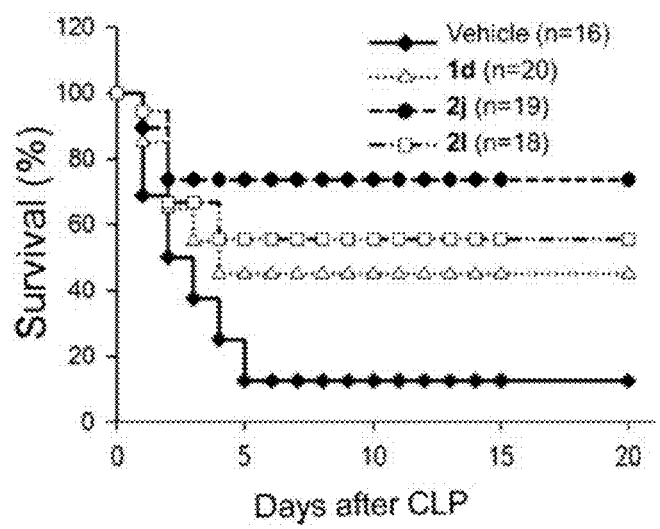
FIG. 10 shows the survival rate of vehicle-, and Compound 1d, 2j and 2l-treated CLP mice.

As shown in FIG. 10, although the survival rate of the vehicle-treated mice group is about 10%, the rate of the 1d-treated mice group is about 45%. Further, the survival rates of the 2j- and 2l-treated mice groups are 74% and 54%, respectively. Thus, the 2j- and 2l-treated mice groups were found to have superior effects on survival rates, compared with the vehicle-treated mice and 1d-trated mice groups.

Further, Compound 1d, 2j and 2l were administered at a daily dose of 10 mg/kg for 21 days after the start of administration of CLP 1 hour before the induction. The serum IL-6 level was measured and is shown in FIG. 11.

Figure 11:
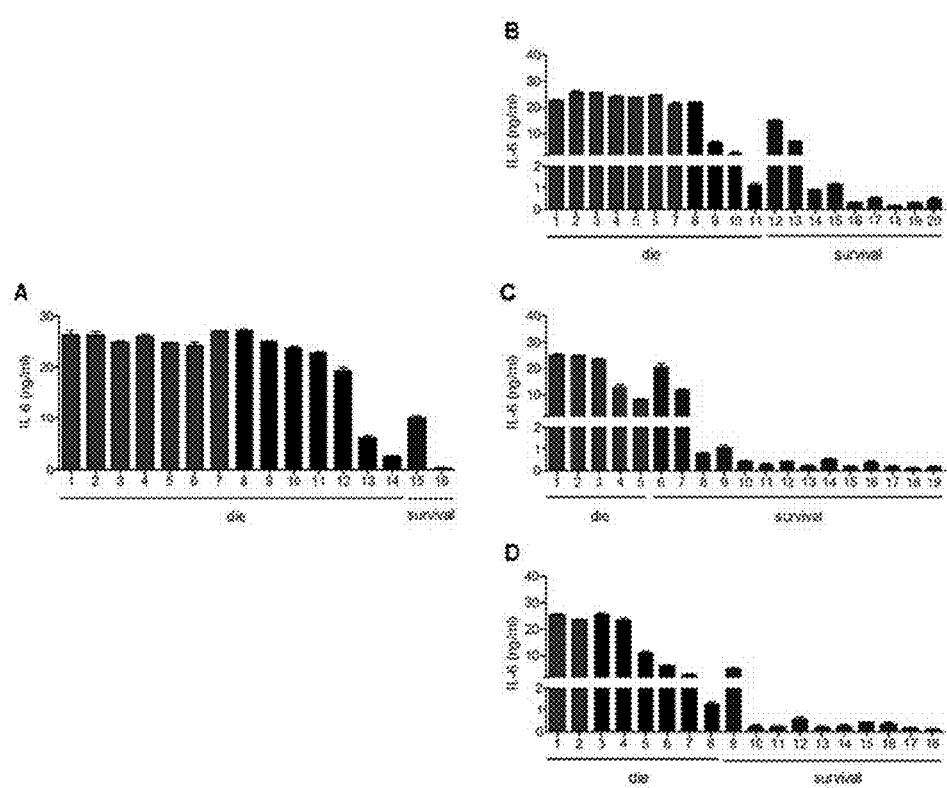
FIG. 11 shows. Shows the serum IL-6 level in vehicle- (A), Compound 1d-treated (B), Compound 2j-treated (C), Compound 2l-treated (C) CLP mice.

As shown in FIG. 11, it is confirmed that the serum IL-6 levels were significantly decreased in the survived mice.

According to the above experimental results, Compounds 2j and 2l showed superior anti-inflammation effects, survival rates and pharmacokinetic properties, when compared with Compound 1d and other compounds having similar structures In addition, it is confirmed that both Compounds 2j and 2l inhibited the translocation of HMGB1 from the nucleus to the cytosol, improved the inhibition of IL-6 release, and regulated the downstream inflammatory signaling pathways.

As a result, it is confirmed that novel Compounds 2j and 2l have an excellent anti-inflammation effect, and can be developed and used as medicines for treating and preventing sepsis.

What is claimed is:

1. A compound represented by [Formula 5], or its pharmaceutically acceptable salt:

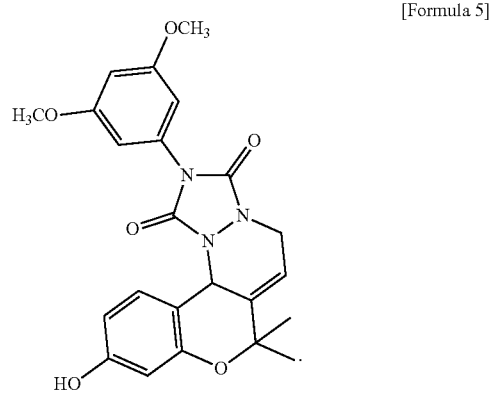 [SMILES: COc1cc(OC)cc(-n2c(=O)n3n(c2=O)C2C(=CC3)C(C)(C)Oc3cc(O)ccc32)c1]

[Formula 5]

2. A method of treating sepsis, gastritis, colitis, rheumatoid arthritis, nephritis, hepatitis and pancreatitis, comprising administering a compound represented by [Formula 3] or its pharmaceutically acceptable salt to a subject in need:

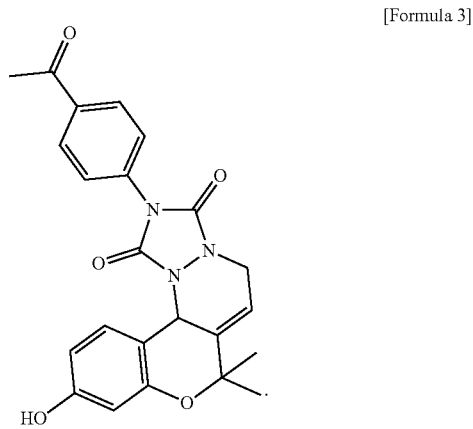 [SMILES: CC(=O)c1ccc(-n2c(=O)n3n(c2=O)C2C(=CC3)C(C)(C)Oc3cc(O)ccc32)cc1]

[Formula 3]

3. A method of treating sepsis, gastritis, colitis, rheumatoid arthritis, nephritis, hepatitis and pancreatitis comprising administering the compound of claim 1 or its pharmaceutically acceptable salt to a subject in need.

* * * * *